US009938278B2

(12) United States Patent
Gege et al.

(10) Patent No.: US 9,938,278 B2
(45) Date of Patent: Apr. 10, 2018

(54) FXR (NR1H4) MODULATING COMPOUNDS

(71) Applicant: Gilead Sciences, Inc., Foster City, CA (US)

(72) Inventors: Christian Gege, Ehingen (DE); Claus Kremoser, Heidelberg (DE); Olaf Kinzel, Heidelberg (DE); Peter A. Blomgren, Issaquah, WA (US); Kevin S. Currie, North Bend, WA (US); Jeffrey E. Kropf, Issaquah, WA (US); Aaron C. Schmitt, Hamden, CT (US); William J. Watkins, Saratoga, CA (US); Jianjun Xu, Seattle, WA (US)

(73) Assignee: GILEAD SCIENCES, INC., Foster City, CA (US)

( * ) Notice: Subject to any disclaimer, the term of this patent is extended or adjusted under 35 U.S.C. 154(b) by 119 days.

(21) Appl. No.: 14/971,825

(22) Filed: Dec. 16, 2015

(65) Prior Publication Data
US 2017/0298068 A1    Oct. 19, 2017

(30) Foreign Application Priority Data

Dec. 17, 2014 (EP) .................................... 14004260

(51) Int. Cl.
| | | |
|---|---|---|
| *A61K 31/506* | (2006.01) | |
| *C07D 471/08* | (2006.01) | |
| *C07D 401/14* | (2006.01) | |
| *C07D 413/14* | (2006.01) | |
| *C07D 261/08* | (2006.01) | |
| *C07D 413/12* | (2006.01) | |
| *C07D 417/14* | (2006.01) | |

(52) U.S. Cl.
CPC ......... *C07D 471/08* (2013.01); *C07D 261/08* (2013.01); *C07D 401/14* (2013.01); *C07D 413/12* (2013.01); *C07D 413/14* (2013.01); *C07D 417/14* (2013.01)

(58) Field of Classification Search
CPC .. C07D 471/08; C07D 261/08; C07D 401/14; C07D 413/12; C07D 413/14; C07D 417/14
See application file for complete search history.

(56) References Cited

U.S. PATENT DOCUMENTS

| | | | | |
|---|---|---|---|---|
| 7,998,995 | B2 * | 8/2011 | Boren | C07D 231/10 514/397 |
| 9,139,539 | B2 * | 9/2015 | Kinzel | C07D 261/08 |
| 9,539,244 | B2 * | 1/2017 | Kinzel | C07D 261/08 |
| 2017/0143684 | A1 * | 5/2017 | Kinzel | C07D 261/08 |
| 2017/0209423 | A1 * | 7/2017 | Notte | A61K 31/4439 |

FOREIGN PATENT DOCUMENTS

| | | |
|---|---|---|
| WO | WO-2009012125 A1 | 1/2009 |
| WO | WO-2009081197 A1 | 7/2009 |
| WO | WO-2012087520 A1 | 6/2012 |
| WO | WO-2012087521 A1 | 6/2012 |
| WO | WO-2013007387 A1 | 1/2013 |
| WO | WO-2016096116 A1 * | 6/2016 ........... C07D 401/14 |

OTHER PUBLICATIONS

Written Opinion and Search Report dated Mar. 1, 2016 for PCT/EP2015/002512.

* cited by examiner

*Primary Examiner* — Alexander R Pagano

(57) ABSTRACT

The present invention relates to compounds which bind to the NR1H4 receptor (FXR) and act as agonists of FXR. The invention further relates to the use of the compounds for the preparation of a medicament for the treatment of diseases and/or conditions through binding of said nuclear receptor by said compounds and to a process for the synthesis of said compounds.

12 Claims, No Drawings

SEQUENCE LISTING

<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: synthetic biotinylated peptide based on
      residues 676-700 of SRC-1 (LCD2, 676-700)

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25

FXR (NR1H4) MODULATING COMPOUNDS

The present invention relates to compounds which bind to the NR1H4 receptor (FXR) and act as agonists or modulators of FXR. The invention further relates to the use of the compounds for the treatment and/or prophylaxis of diseases and/or conditions through binding of said nuclear receptor by said compounds.

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface (D. J. Mangelsdorf et al., Cell 1995, 83, 835; R. M. Evans, Mol. Endocrinol. 2005, 19, 1429).

In general, three functional domains have been defined in NRs. An amino terminal domain is believed to have some regulatory function. It is followed by a DNA-binding domain hereinafter referred to as "DBD" which usually comprises two zinc finger elements and recognizes a specific Hormone Responsive Element hereinafter referred to as "HRE" within the promoters of responsive genes. Specific amino acid residues in the "DBD" have been shown to confer DNA sequence binding specificity (M. Schena and K. R. Yamamoto, Science 1988, 241, 965). A ligand-binding-domain hereinafter referred to as "LBD" is at the carboxy-terminal region of known NRs.

In the absence of hormone, the LBD appears to interfere with the interaction of the DBD with its HRE. Hormone binding seems to result in a conformational change in the NR and thus opens this interference (A. M. Brzozowski et al., Nature 1997, 389, 753). A NR without the LBD constitutively activates transcription but at a low level.

Coactivators or transcriptional activators are proposed to bridge between sequence specific transcription factors, the basal transcription machinery and in addition to influence the chromatin structure of a target cell. Several proteins like SRC-1, ACTR, and Grip1 interact with NRs in a ligand enhanced manner (D. M. Heery et al., Nature 1997, 387, 733; T. Heinzel et al., Nature 1997, 387, 43; K. W. Nettles and G. L. Greene, Annu. Rev. Physiol. 2005, 67, 309).

Nuclear receptor modulators like steroid hormones affect the growth and function of specific cells by binding to intracellular receptors and forming nuclear receptor-ligand complexes. Nuclear receptor-hormone complexes then interact with a HRE in the control region of specific genes and alter specific gene expression (A. Aranda and A. Pascual, Physiol. Rev. 2001, 81, 1269).

The Farnesoid X Receptor alpha (hereinafter also often referred to as NR1H4 when referring to the human receptor) is a prototypical type 2 nuclear receptor which activates genes upon binding to promoter region of target genes in a heterodimeric fashion with Retinoid X Receptor (B. M. Forman et al., Cell 1995, 81, 687). The relevant physiological ligands of NR1H4 are bile acids (D. J. Parks et al., Science 1999, 284, 1365; M. Makishima et al., Science 1999, 284, 1362). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signalling by upregulating the expression of the cytokine Fibroblast Growth Factor 15 (rodents) or 19 (monkeys, humans, J. A. Holt et al., Genes Dev. 2003, 17, 1581; T. Inagaki et al., Cell Metab. 2005, 2, 217).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539, WO 2008/025540, WO 2008/157270, WO 2009/005998, WO 2009/012125, WO 2011/020615, WO 2012/087519, WO 2012/087520 and WO 2012/087521. Further small molecule FXR modulators have been recently reviewed (M. L. Crawley, Expert Opin Ther. Pat. 2010, 20, 1047; D. Merk et al., Future Med. Chem. 2012, 4, 1015 and C. Gege et al., Curr. Top. Med. Chem. 2014, 14, 2143).

In WO 2013/007387 we disclosed hydroxy containing cyclobutyl and azetidine derivatives of the following general formula

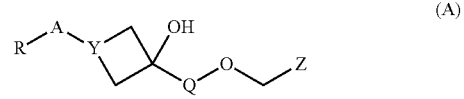

(A)

wherein the variables are defined similar as in this application.

Although numerous FXR agonists are disclosed to date, here is still a need to deliver improved FXR agonist.

Said problem has been solved by a compound according to the following Formula (1), an enantiomer, diastereomer, tautomer, solvate, prodrug or pharmaceutical acceptable salt thereof

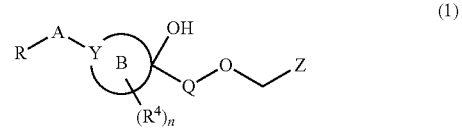

(1)

wherein
R is selected from the group consisting of hydrogen, halogen, $C_{1-6}$-alkyl, $C_{2-6}$-alkenyl, $C_{2-6}$-alkynyl, halo-$C_{1-6}$-alkyl, $C_{0-6}$-alkylene-O—$R^7$, $C_{0-6}$-alkylene-CN, $C_{0-6}$-alkylene- NR⁷R⁸, O—C₃₋₁₀-cycloalkyl, O—C₁₋₆-alkylene-O—R⁷, O—C₃₋₁₀-heterocycloalkyl, C₀₋₆-alkylene-CO₂R⁷, C₀₋₆-alkylene-C(O)R⁷, C₀₋₆-alkylene-C(O)NR⁷R⁸, C₀₋₆-alkylene-C(O)NR⁷SO₂R⁷, C₀₋₆-alkylene-N(R⁷)C(O)R⁷, C₀₋₆-alkylene-SO$_x$—R⁷, C₀₋₆-alkylene-SO₃H, C₀₋₆-alkylene-SO₂—NR⁷R⁸, C₀₋₆-alkylene-SO₂—NR⁸COR⁷, C₀₋₆-alkylene-N(R⁷)SO₂—R⁸, and C₀₋₆-alkylene-SO₂—C₃₋₁₀-heterocycloalkyl, wherein alkylene, cycloalkyl, heterocycloalkyl and the 5- or 6-membered heteroaryl are unsubstituted or substituted by 1 to 4 substituents independently selected from the group consisting of halogen, CN, C₁₋₃-alkyl, halo-C₁₋₃-alkyl, OH, oxo, CO₂H, SO₃H, O—C₁₋₃-alkyl and O-halo-C₁₋₃-alkyl;

R⁷ is independently selected from the group consisting of hydrogen, C₁₋₆-alkyl, halo-C₁₋₆-alkyl, C₀₋₆-alkylene-C₃₋₈-cycloalkyl, C₀₋₆-alkylene-C₃₋₈-heterocycloalkyl, 5- or 6-membered heteroaryl and phenyl, wherein alkyl, alkylene, cycloalkyl, heterocycloalkyl, phenyl and heteroaryl are unsubstituted or substituted with 1 to 6 substituents independently selected from the group consisting of halogen, CN, OH, oxo, CO₂H, C₁₋₃-alkyl, halo-C₁₋₃-alkyl, O—C₁₋₃-alkyl, O-halo-C₁₋₃-alkyl, SO₃H and SO₂—C₁₋₃-alkyl;

R⁸ is independently selected from the group consisting of hydrogen, C₁₋₆-alkyl, halo-C₁₋₆-alkyl and C₃₋₆-cycloalkyl;

or R⁷ and R⁸ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, C₁₋₄-alkyl and halo-C₁₋₄alkyl;

A is a 6-10 membered mono- or bicyclic aryl or a 5-10 membered mono- or bicyclic heteroaryl containing 1 to 5 heteroatoms independently selected from the group consisting of N, O and S, wherein aryl and heteroaryl are unsubstituted or substituted with one or two groups independently selected from the group consisting of OH, halogen, CN, O—C₁₋₆-alkyl, O-halo-C₁₋₆-alkyl, C₁₋₆-alkyl, halo-C₁₋₆-alkyl, C₃₋₆-cycloalkyl and halo-C₃₋₆-cycloalkyl;

B is a C₅₋₈-cycloalkyl ring or, if Y is N, then is B a C₅₋₈-heterocycloalkyl containing one nitrogen atom, and wherein the substituent Q is not directly adjacent to substituent A;

Q is selected from the group consisting of phenyl, pyridyl, thiazolyl, thiophenyl, pyrimidyl, oxazolyl, pyrazolyl, imidazolyl and triazolyl, each unsubstituted or substituted with one or two groups independently selected from the group consisting of halogen, C₁₋₄-alkyl, halo-C₁₋₄-alkyl, C₁₋₄-alkoxy or halo-C₁₋₄-alkoxy;

Y is selected from N, CH or CF;

Z is selected from

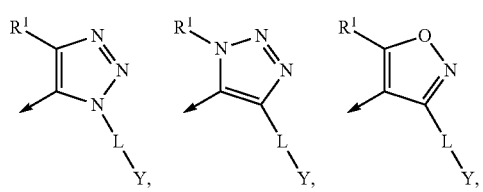

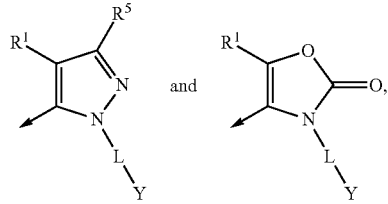

wherein
L is selected from the group consisting of a bond, C₁₋₃-alkylene and C₁₋₃-alkylene-O—;
Y is selected from phenyl, pyridyl, pyridyl-N-oxide, pyrimidyl, pyridinonyl, pyrimidinonyl, C₄₋₈-cycloalkyl and C₄₋₈-heterocycloalkyl, wherein phenyl, pyridyl, pyridyl-N-oxide, pyrimidyl, pyridinonyl, pyrimidinonyl, C₄₋₈-cycloalkyl and C₄₋₈-heterocycloalkyl are substituted with R² and R³ and optionally substituted one or two times with a group selected from fluoro, chloro, CN, NH₂, NH(C₁₋₃-alkyl), N(C₁₋₃-alkyl)₂, C₁₋₃-alkyl, fluoro-C₁₋₃-alkyl, OH, C₁₋₃-alkoxy, fluoro-C₁₋₃-alkoxy, C₃₋₆-cycloalkyl and fluoro-C₃₋₆-cycloalkyl;
R¹ is selected from the group consisting of C₁₋₄-alkyl and C₃₋₆-cycloalkyl, wherein C₁₋₄-alkyl is unsubstituted or substituted with 1 to 3 substituents independently selected from the group consisting of fluoro, hydroxy, C₁₋₃-alkoxy and fluoro-C₁₋₃-alkoxy, and C₃₋₆-cycloalkyl is unsubstituted or substituted with 1 to 3 substituents independently selected from the group consisting of fluoro, hydroxy, C₁₋₃-alkyl, fluoro-C₁₋₃-alkyl, C₁₋₃-alkoxy and fluoro-C₁₋₃-alkoxy;
R² and R³ are independently selected from the group consisting of hydrogen, halogen, C₁₋₃-alkyl, halo-C₁₋₃-alkyl, C₁₋₃-alkoxy, halo-C₁₋₃-alkoxy, cyclopropyl and fluoro-cyclopropyl;
R⁴ is independently selected from halogen, C₁₋₃-alkyl, halo-C₁₋₃-alkyl, C₁₋₃-alkoxy, halo-C₁₋₃-alkoxy, C₃₋₆-cycloalkyl, and fluoro-C₃₋₆-cycloalkyl;
R⁵ is selected from the group consisting of hydrogen, fluoro, CH₃, CHF₂ and CF₃;
n is selected from 0, 1, 2, 3 and 4; and
x is selected from 0, 1 and 2.

In another embodiment, the present invention is directed to a compound according to Formula (1) as a medicament.

In a further embodiment, the present invention is directed to a compound according to Formula (1) for use in the prophylaxis and/or treatment of diseases mediated by FXR.

In another embodiment, the present invention is directed to the use of a compound according to Formula (1) for the preparation of a medicament for the prophylaxis and/or treatment of diseases mediated by FXR.

In yet a further embodiment, the present invention relates to a method for treating or preventing diseases mediated by FXR in a subject in need thereof, the method comprising administering an effective amount of a compound according to Formula (1) to the subject.

In another embodiment in combination with any of the above or below embodiments, the disease is selected from chronic intrahepatic or some forms of extrahepatic cholestatic conditions; liver fibrosis; obstructive or chronic inflammatory disorders of the liver; liver cirrhosis; liver steatosis and associated syndromes, cholestatic or fibrotic effects that are associated with alcohol-induced cirrhosis or with viral-borne forms of hepatitis; liver failure or liver ischemia after major liver resection; chemotherapy associated steatohepatitis (CASH); acute liver failure; and/or Inflammatory Bowel Diseases.

In another embodiment in combination with any of the above or below embodiments, the disease is selected from lipid and lipoprotein disorders; Type II Diabetes and clinical complications of Type I and Type II Diabetes, including diabetic nephropathy, diabetic neuropathy, diabetic retinopathy and other observed effects of clinically manifest long term Diabetes; conditions and diseases which result from chronic fatty and fibrotic degeneration of organs due to enforced lipid and specifically triglyceride accumulation and subsequent activation of profibrotic pathways, such as Non-Alcoholic Fatty Liver Disease (NAFLD), or Non-Alcoholic Steatohepatitis (NASH); obesity or metabolic syndrome (combined conditions of dyslipidemia, diabetes or abnormally high body-mass index); and/or cute myocardial infarction, acute stroke or thrombosis which occurs as an endpoint of chronic obstructive atherosclerosis.

In another embodiment in combination with any of the above or below embodiments, the disease is selected from non-malignant hyperproliferative disorders and malignant hyperproliferative disorders, specifically of hepatocellular carcinoma, colon adenoma and polyposis, colon adenocarcinoma, breast cancer, pancreas adenocarcinoma, Barrett's esophagus or other forms of neoplastic diseases of the gastrointestinal tract and the liver.

The compounds of the present invention share a common chemical structure according to Formula (1) in claim 1.

In a preferred embodiment in combination with any of the above or below embodiments, R in Formula (1) is selected from the group consisting of $CO_2H$, $SO_3H$, $CONR^7R^8$, tetrazolyl, 1,2,4-oxadiazol-5(4H)-one-3-yl and $SO_2NHCOR^7$.

In a further preferred embodiment in combination with any of the above or below embodiments, $R^7$ is selected from the group consisting of hydrogen, $C_{1-6}$-alkyl, halo-$C_{1-6}$-alkyl, $C_{1-6}$-alkylene-$R^9$, $SO_2$—$C_{1-3}$-alkyl.

In a preferred embodiment in combination with any of the above or below embodiments, $R^8$ is selected from the group consisting of hydrogen, $C_{1-6}$-alkyl, halo-$C_{1-6}$-alkyl.

In another preferred embodiment in combination with any of the above or below embodiments, $R^9$ is selected from the group consisting of COOH, OH and $SO_3H$.

In a preferred embodiment in combination with any of the above or below embodiments, A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, oxazolyl, naphthyl, quinolyl, isoquinolyl, benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl.

In a further preferred embodiment in combination with any of the above or below embodiments, R-A is selected from

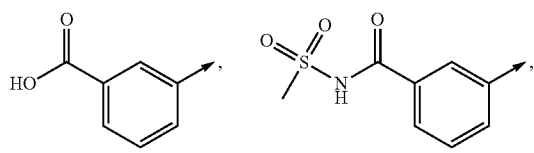

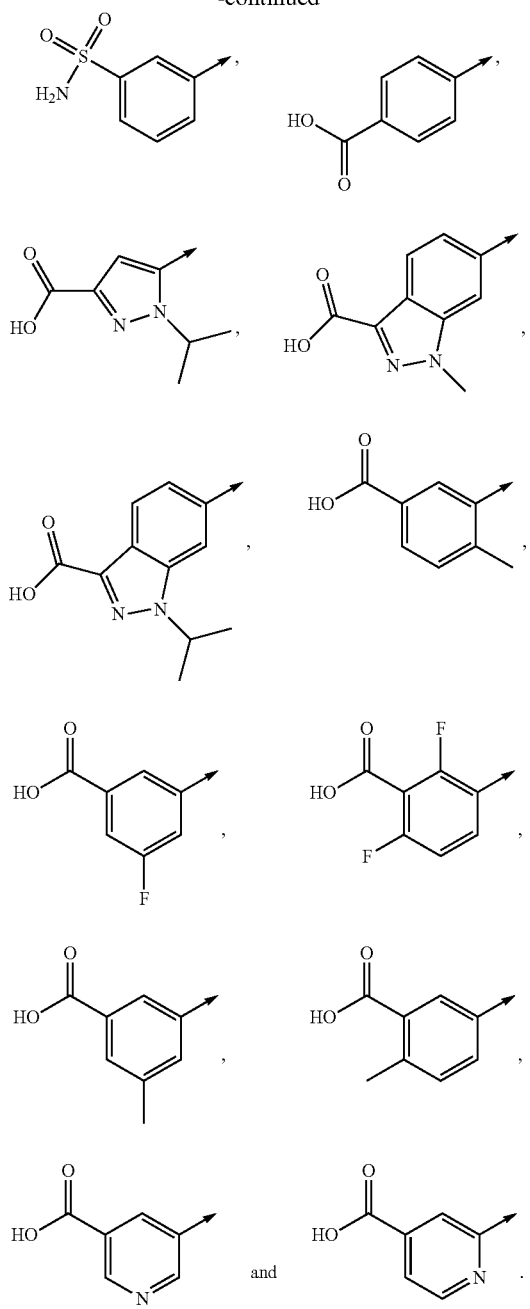

In a further preferred embodiment in combination with any of the above or below embodiments, Z is selected from

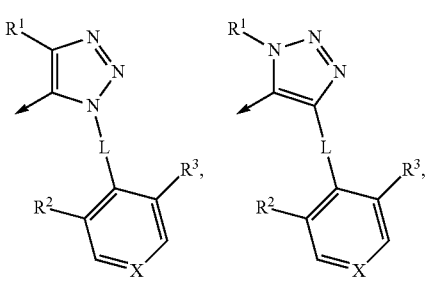

-continued

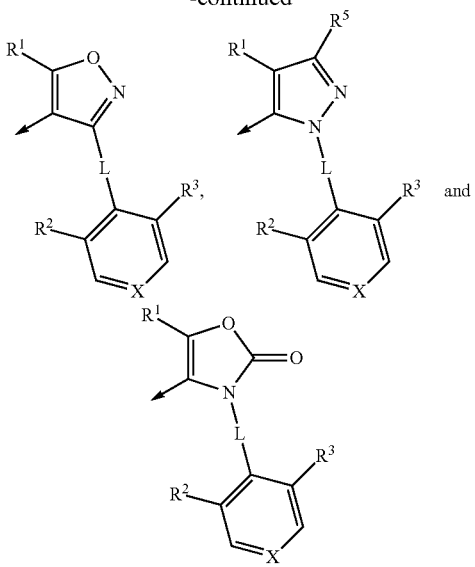

wherein
L is selected from the group consisting of a bond, $C_{1-3}$-alkylene and $C_{1-3}$-alkylene-O—;
X is selected from the group consisting of CH, CF, N and NO;
$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_{3-6}$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;
$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl; and
$R^5$ is selected from the group consisting of hydrogen, fluoro, $CH_3$, $CHF_2$ and $CF_3$.

In a more preferred embodiment in combination with any of the above or below embodiments, Z is selected from

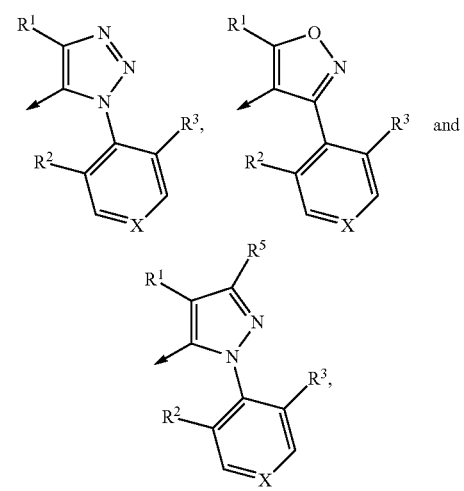

wherein
X is selected from the group consisting of CH, CF, N and NO;

$R^1$ is selected from the group consisting of $CF_3$, $CHF_2$, isopropyl and cyclopropyl, wherein isopropyl and cyclopropyl are unsubstituted or substituted with one or two fluoro or one hydroxy;
$R^2$ is selected from the group consisting of fluoro, chloro, $CH_3$, $CHF_2$, $CF_3$, $OCHF_2$ and $OCF_3$;
$R^3$ is selected from the group consisting of hydrogen, fluoro, chloro, $CH_3$, $CHF_2$, $CF_3$, $OCHF_2$ and $OCF_3$; and
$R^5$ is selected from the group consisting of hydrogen, fluoro, $CH_3$, $CHF_2$ and $CF_3$.

In a further preferred embodiment in combination with any of the above or below embodiments, the moiety

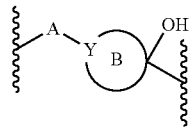

is selected from

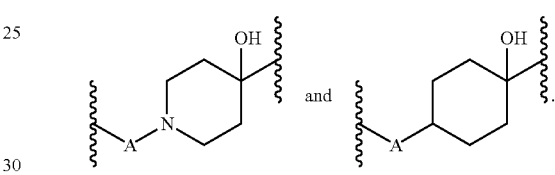

In a more preferred embodiment, the compound is according to Formula (2)

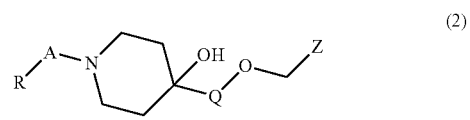

wherein
A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, oxazolyl, naphthyl, quinolyl, isoquinolyl, benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl;
R is selected from the group consisting of $CO_2H$, $SO_3H$, $CONR^7R^8$, tetrazolyl, 1,2,4-oxadiazol-5(4H)-one-3-yl and $SO_2NHCOR^7$, wherein
 $R^7$ selected from the group consisting of hydrogen, $C_{1-6}$-alkyl, halo-$C_{1-6}$-alkyl, $C_{1-6}$-alkylene-$R^9$, $SO_2$—$C_{1-6}$-alkyl;
 $R^8$ selected from the group consisting of hydrogen, $C_{1-6}$-alkyl, halo-$C_{1-6}$-alkyl; and
 $R^9$ is selected from the group consisting of COOH, OH and $SO_3H$;
Q is selected from the group consisting of phenyl, pyridyl, thiazolyl, thiophenyl and pyrimidyl, each unsubstituted or substituted with one or two groups independently selected from the group consisting of fluoro, chloro, $CH_3$, $CHF_2$ and $CF_3$;

Z is selected from

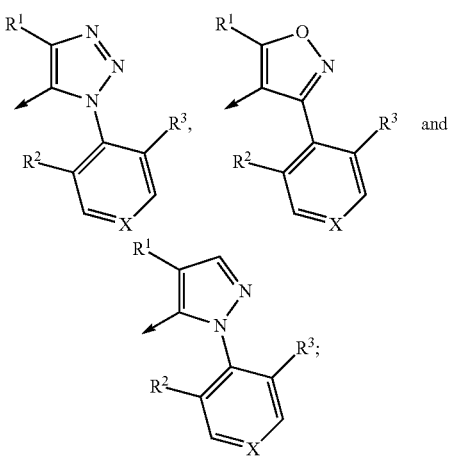

X is selected from the group consisting of CH, N and NO;
$R^1$ is selected from the group consisting of isopropyl and cyclopropyl, wherein isopropyl and cyclopropyl are unsubstituted or substituted with one or two fluoro or one hydroxy;
$R^2$ is selected from the group consisting of fluoro, chloro, $CH_3$, $CHF_2$, $CF_3$, $OCHF_2$ and $OCF_3$; and
$R^3$ is selected from the group consisting of hydrogen, fluoro, chloro, $CH_3$, $CHF_2$, $CF_3$, $OCHF_2$ and $OCF_3$.

In the context of the present invention "$C_{1-6}$-alkyl" means a saturated alkyl chain having 1 to 6 carbon atoms which may be straight chained or branched. Examples thereof include methyl, ethyl, propyl, isopropyl, n-butyl, isobutyl, tert-butyl, n-pentyl, isopentyl, neopentyl and hexyl.

The term "halo-$C_{1-6}$-alkyl" means that one or more hydrogen atoms in the alkyl chain are replaced by a halogen. A preferred example thereof is $CF_3$.

"$C_{2-6}$-alkenyl" means an alkyl chain having 1 to 6 carbon atoms which may be straight chained or branched, containing at least one carbon to carbon double bond. Examples thereof include ethenyl, propenyl, butenyl, pentenyl, hexenyl or (1E,3Z)-2-methylpenta-1,3-dien-1-yl. Preferred examples are ethenyl, propenyl or (1E,3Z)-2-methylpenta-1,3-dien-1-yl.

"$C_{2-6}$-alkynyl" means an alkyl chain having 1 to 6 carbon atoms which may be straight chained or branched, containing at least one carbon to carbon triple bond. Examples thereof include ethynyl, propynyl, 1-butynyl, 2-butynyl, 1-pentynyl, 2-pentynyl, 1-hexynyl, 2-hexynyl or 3-hexynyl. Preferred examples thereof include ethynyl and propynyl.

A "$C_{0-6}$-alkylene" means that the respective group is divalent and connects the attached residue with the remaining part of the molecule. Moreover, in the context of the present invention, "$C_0$-alkylene" is meant to represent a bond.

A $C_{5-10}$-cycloalkyl group means a saturated or partially unsaturated mono-, bi- or spirocyclic ring system comprising 5 to 10 carbon atoms. Examples include cyclopentyl, cyclohexyl, cyclohexenyl, bicyclo[2.2.2]octyl, bicyclo[3.2.1]octanyl, spiro[3.3]heptyl, bicyclo[2.2.1]heptyl, adamantyl and pentacyclo[4.2.0.0$^{2,5}$.0$^{3,8}$.0$^{4,7}$]octyl.

A $C_{3-10}$-heterocycloalkyl group means a saturated or partially unsaturated 3 to 10 membered carbon mono-, bi- or spirocyclic ring wherein 1, 2 or 3 carbon atoms are replaced by 1, 2 or 3 heteroatoms, respectively, wherein the heteroatoms are independently selected from N, O, S, SO and $SO_2$.

Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected with the remaining part of the molecule via a carbon or nitrogen atom.

A 5-10-membered mono- or bicyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzofuranyl, benzoxazolyl, indolyl, indolizinyl and pyrazolo[1,5-a]pyrimidinyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

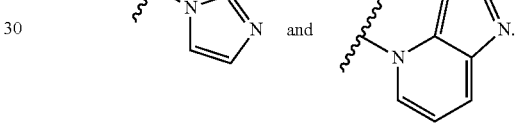

A 6-10-membered mono- or bicyclic aromatic ring system (within the application also referred to as aryl) means an aromatic carbon cycle such as phenyl or naphthalenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine, more preferably fluorine or chlorine and most preferably fluorine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

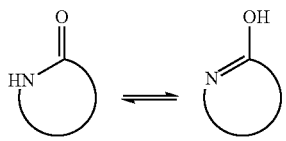

A $C_{3-6}$-cycloalkyl or $C_{3-6}$-heterocycloalkyl group can be connected straight or spirocyclic, e.g. when cyclohexane is substituted with the heterocycloalkyl group oxetane, the following structures are possible:

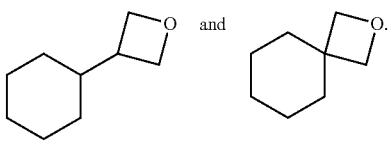 [SMILES: C1CCC(C2COC2)CC1 ; C1CCC2(CC1)COC2]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carboxylate in a compound of the present invention is, for example, converted into an alkyl-, aryl-, choline-, amino, acyloxymethylester, linolenoylester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient.

They may be conveniently presented in unit dosage form and prepared by any of the methods well-known in the art of pharmacy.

General Schemes

The compounds of the present invention can be prepared according to schemes I-III. As depicted in Scheme I an alicyclic ketone, substituted with substituent A can react with a metalated aromatic or heteroaromatic ring M-Q-O—CH$_2$Z (M=metal, e.g. Li) in aprotic solvents and preferably at low temperatures to afford a hydroxyl substituted alicycle bearing the substituents A and Q. In the case where Y is CH two isomers can form (A and Q transannular cis or trans to each other). Under optimized conditions the formation of mainly one of the two isomers can be achieved. The two isomers can be separated by appropriate methods known in the art like e.g. silica gel chromatography or preparative RP-HPLC.

Scheme I

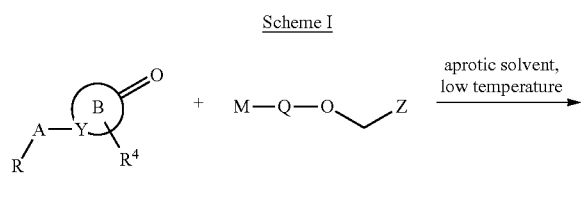

In Scheme II is depicted a methods which are used to prepare the cyclic ketones needed for the synthesis of the compounds of this invention. In cases where Y is nitrogen, Cu- or Pd-catalysed C—N cross coupling between cyclic amines and halo-aromatic or halo-heteroaromatic rings afford the corresponding N-substituted cyclic amines bearing a functionality which later can be transformed into a keto group.

Scheme II

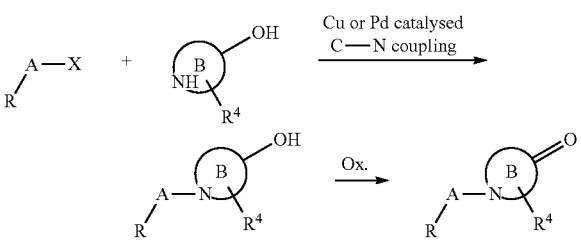

In the case where moiety A is a pyrazole an alternative synthetic route to the compounds of the invention is illustrated in scheme III. Acetyl bearing intermediates a1 can react with oxalic esters in the presence of strong bases to form ketoesters a2. These can undergo a cyclysation with alkyl hydrazines under promotion of Lawesson's reagent to form pyrazole intermediates a3. Intermediates a3 can be transformed into cyclic ketones (a4) which can undergo an addition reaction according to scheme I and after final ester hydrolysis afford pyrazole analogs of compounds of the present invention.

Scheme III

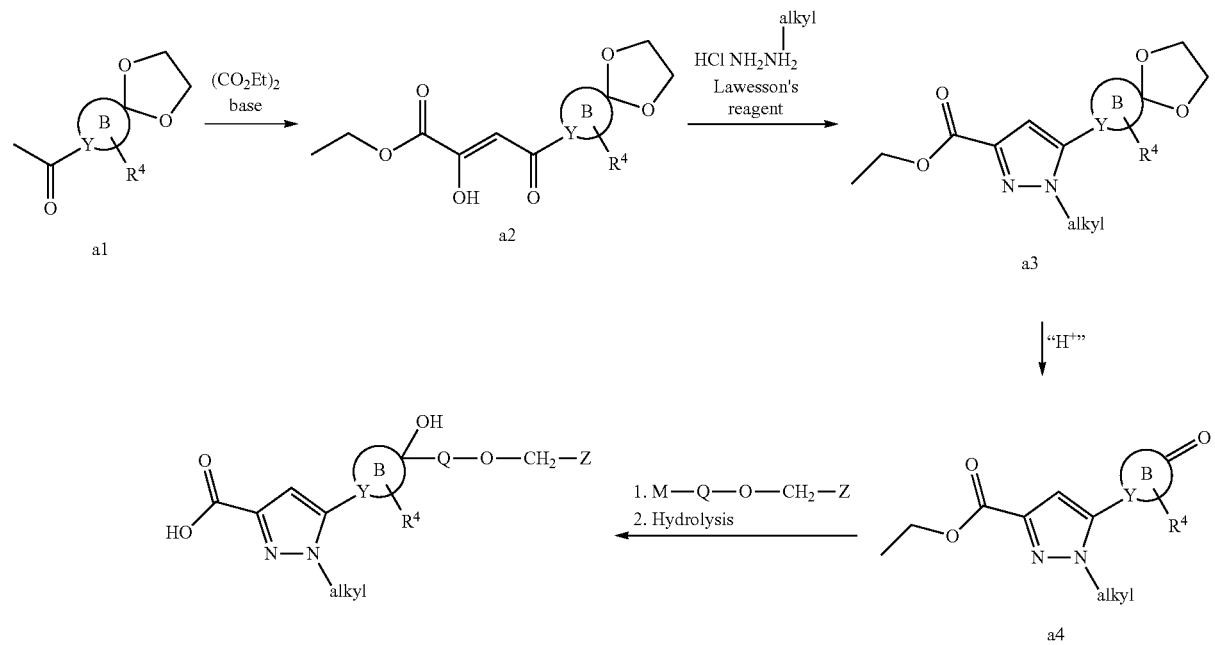

As a result, the present invention relates to compounds according to the general Formula (1) which bind to FXR and act as agonists or modulators of FXR.

The invention further relates to the use of said compounds for the treatment and/or prophylaxis of diseases and/or conditions through binding of said nuclear receptor by said compounds. Further the present invention relates to the use of said compounds for the preparation of a medicament for the treatment and/or prophylaxis of diseases and/or conditions through binding of said nuclear receptor by said compounds. Specifically, the present invention relates to the use of compounds according to Formula (1) in the preparation of a medicament for the prophylaxis and/or treatment of chronic intrahepatic or some forms of extrahepatic cholestatic conditions, of liver fibrosis, of acute intrahepatic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistant infections by intracellular bacteria or parasitic protozoae, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis.

Medicaments as referred to herein may be prepared by conventional processes, including the combination of a compound according to the present invention and a pharmaceutically acceptable carrier.

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (T. Claudel et al., Arterioscler. Thromb. Vasc. Biol. 2005, 25, 2020; Y. D. Wang et al., Cell Res. 2008, 18, 1087.

FXR regulates a complex pattern of response genes in the liver and in the gastrointestinal tract. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or CDCA, this can be regarded as an example of feedback inhibition on the gene expression level (B. Goodwin et al., Mol. Cell 2000, 6, 517; T. T. Lu et al., Mol. Cell 2000, 6, 507). Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice (C. J. Sinai et al., Cell 2000, 102, 731). where under- or overexpression of several ABC-transporters in the liver was shown. Further detailed analysis revealed that the major bile salt excretory pump BSEP or ABCB11 (M. Ananthanarayanan et al., J. Biol. Chem. 2001, 276, 28857; J. R. Plass et al., Hepatology 2002, 35, 589) as well as the key enzyme which mediates lipid transfer from lipoproteins to phospholipids, PLTP (N. L. Urizar et al., J. Biol. Chem. 2000, 275, 39313), and the two key canalicular membrane transporters for phospholipids, MRP-2 (ABCC4) (H. R. Kast et al., J. Biol. Chem. 2002, 277, 2908) and MDR-3 (ABCB4); L. Huang et al., J. Biol. Chem. 2003, 278, 51085) are direct targets for ligand-directed transcriptional activation by FXR (summarized in: M. Miyata, J. Pharmacol. Exp. Ther. 2005, 312, 759; G. Rizzo et al., Curr. Drug Targets Immune Endocr. Metabol. Disord. 2005, 5, 289).

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 (P. R. Maloney et al., J. Med. Chem. 2000, 43, 2971; T. M. Willson et al., Med. Res. Rev. 2001, 21, 513) as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated (R. Pellicciari et al., J. Med. Chem. 2002, 45, 3569; Y. Liu et al., J. Clin. Invest. 2003, 112, 1678). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 in hepatic stellate cells and the subsequent reduction of alpha-collagen mRNA and Transforming growth factor beta (TGF-beta) mRNA which are both pro-fibrotic factors by FXR agonists (S. Fiorucci et al., Gastroenterology 2004, 127, 1497; S. Fiorucci et al., J. Pharmacol. Exp. Ther. 2005, 314, 584). Furthermore, anti-cholestatic activity was demonstrated in bile-duct ligated animal models as well as in animal models of estrogen-induced cholestasis (S. Fiorucci et al., J. Pharmacol. Exp. Ther. 2005, 313, 604).

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al., Gastroenterology 2004, 126, 756; L. Alvarez et al., Hum. Mol. Genet. 2004, 13, 2451) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: G. Rizzo et al., Curr. Drug Targets Immune Endocr. Metabol. Disord. 2005, 5, 289; G. Zollner et al., Mol. Pharm. 2006, 3, 231; S. Y. Cai et al., Expert Opin. Ther. Targets 2006, 10, 409).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease (H. Wittenburg, Gastroenterology 2003, 125, 868). Using the synthetic FXR tool compound GW4064 it could be demonstrated that activation of FXR leads to an improvement of the Cholesterol Saturation Index (CSI) and directly to an abolishment of gallstone formation in C57L gallstone susceptible mice whereas drug treatment in FXR knockout mice shows no effect on gallstone formation (A. Moschetta et al., Nature Medicine 2004, 10, 1352).

These results qualify FXR as a good target for the development of small molecule agonists that can be used to prevent cholesterol gallstone formation or to prevent re-formation of gallstones after surgical removal or shockwave lithotripsy (discussed in: S. A. Doggrell, Curr. Opin. Investig. Drugs 2006, 7, 344).

Thus, in one embodiment of the invention, the compound according to Formula (1) and pharmaceutical compositions comprising said compound is used for the prophylaxis and/or treatment of obstructive or chronic inflammatory disorders that arise out of improper bile composition such as cholelithiasis also known as cholesterol gallstones.

Beyond its strong hepatoprotective and choleretic as well as anti-fibrotic effects that FXR shows upon small molecule stimulated activation in the liver, FXR seems to have a role in protecting the intestine from neoplastic transformation and from the development of polyps and their transition into adenocarcinoma in the gut (S. Modica et al., Cancer Res. 2008, 68, 9589 and R. R. Maran et al., J. Pharmacol. Exp. Ther. 2009, 328, 469). Similar to the situation in the intestine absence of FXR leads to a high increase in the formation of Hepatocellular Cacrcinoma (HCC), the most prominent form of liver cancer (I. Kim et al., Carcinogenesis 2007, 28, 940 and F. Yang et al., Cancer Res. 2007, 67, 863). Whereas a functional FXR prevents the formation of colon adenocarcinoma and hepatocellular carcinoma, FXR activation induces liver regeneration after hepatectomy (W. Huang et al., Science 2006, 312, 233).

The combined hepatoprotective, anti-neoplastic and liver regenerative effects associated with FXR activation can be therapeutically exploited for the use of FXR agonists in the treatment of sever liver diseases. In one embodiment, the compounds according to the invention and pharmaceutical compositions comprising said compounds are used in the treatment of liver diseases such as HCC, stimulation of liver regrowth and amelioration of side effects associated with major liver resection, liver cirrhosis independent of the etiology and prevention or treatment of liver ischemia in the course of liver transplantation or major liver surgery.

Since the discovery of the first synthetic FXR agonist and its administration to rodents it became evident that FXR is a key regulator of serum triglycerides (P. Maloney et al., J. Med. Chem. 2000, 43, 2971; T. Willson et al., Med. Res. Rev. 2001, 21, 513). Over the past six years accumulating evidence has been published that activation of FXR by synthetic agonists leads to significant reduction of serum triglycerides, mainly in the form of reduced VLDL, but also to reduced total serum cholesterol (H. R. Kast et al., Mol. Endocrinol. 2001, 15, 1720; N. L. Urizar et al., Science 2002, 296, 1703; G. Lambert et al., J. Biol. Chem. 2003, 278, 2563; M. Watanabe et al., J. Clin. Invest. 2004, 113, 1408; A. Figge et al., J. Biol. Chem. 2004, 279, 2790; S. Bilz et al., Am. J. Physiol. Endocrinol. Metab. 2006, 290, E716).

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (K. R. Stayrook et al., Endocrinology 2005, 146, 984; Y. Zhang et al., PNAS 2006, 103, 1006; B. Cariou et al., J. Biol. Chem. 2006, 281, 11039; K. Ma et al., J. Clin. Invest. 2006, 116, 1102; D. Duran-Sandoval et al., Biochimie 2005, 87, 93). An effect on reduction of body weight was also recently observed in mice overfed with a high lipid diet (C. Lihong et al., American Diabetes Association (ADA) $66^{th}$ annual scientific sessions, June 2006, Abstract Number 856-P). This weight loss effect might results from FXR's induction of FGF-19, a fibroblast growth factor that is known to lead to weight loss and athletic phenotype (J. Holt et al., Genes Dev. 2003, 17, 1581; E. Tomlinson et al., Endocrinology 2002, 143, 1741). In recent patent applications, the effect of FXR agonist on reduction of body weight was demonstrated (WO 2004/087076; WO 2003/080803).

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the invention and pharmaceutical compositions comprising said compounds are used in the prophylaxis and/or treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the prophylaxis and/or treatment of chronic intrahepatic, such as PBC, PSC, progressive familiar cholestasis (PFIC), alcohol-induced cirrhosis and associated cholestasis, and some forms of extrahepatic cholestatic conditions, or liver fibrosis.

The invention also relates to a compound of Formula (1) or to a pharmaceutical composition comprising said compound for the prophylaxis and/or treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for preventing and/or treating a disease selected from the group consisting of lipid and lipoprotein disorders such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the prophylaxis and/or treatment of diseases where the combined lipid lowering, anti-cholestatic and anti-fibrotic effects of FXR-targeted medicaments can be exploited for the treatment of liver steatosis and associated syndromes such as NASH, or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice (E. A. Hanniman et al., J. Lipid Res. 2005, 46, 2595). Therefore, FXR agonists might have clinical utility as anti-atherosclerotic and cardioprotective drugs. The downregulation of Endothelin-1 in Vascular Smooth Muscle Cells might also contribute to such beneficial therapeutic effects (F. He et al., Circ. Res. 2006, 98, 192).

The invention also relates to a compound according to Formula (1) or a pharmaceutical composition comprising said compound for preventive and posttraumatic treatment of cardiovascular disorders such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells (K. E. Swales et al., Cancer Res. 2006, 66, 10120 and F. Journe et al., Breast Cancer Res. Treat. 2009, 115, 523).

This would allow to regard FXR also as a potential target for the treatment of proliferative diseases, especially metastasizing cancer forms that express a small molecule responsive form of FXR.

In a further embodiment, said compounds and pharmaceutical compositions are used for the prophylaxis and/or treatment of malignant hyperproliferative disorders such as different forms of cancer, specifically certain forms of breast, liver or colon cancer where interference with an FXR ligand will have a beneficial impact.

Finally, FXR seems also to be involved in the control of antibacterial defense in the intestine (T. Inagaki et al., PNAS. 2006, 103, 3920) although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the invention also relates to a compound according to Formula (1) or a pharmaceutical composition comprising said compound for preventing and/or treating a disease related to Inflammatory Bowel Diseases such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the prophylaxis and/or treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In a further embodiment, the compounds or pharmaceutical composition of the present invention are useful in preventing and/or treating clinical complications of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of Diabetes are also encompassed by the present invention.

Furthermore, conditions and diseases which result from chronic fatty and fibrotic degeneration of organs due to enforced lipid and specifically triglyceride accumulation and subsequent activation of profibrotic pathways may also be prevented and/or treated by applying the compounds or pharmaceutical composition of the present invention. Such conditions and diseases encompass NASH and chronic cholestatic conditions in the liver, Glomerulosclerosis and Diabetic Nephropathy in the kidney, Macula Degeneration and Diabetic Retinopathy in the eye and Neurodegenerative diseases such as Alzheimer's Disease in the brain, or Diabetic Neuropathies in the peripheral nervous system.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid;

a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Since the compounds of the present invention mostly represent carboxylic acids or similar anionic isosters thereof, and since it is well known that salt forms of ionic drug compounds can substantially affect the bioavailability of drug compounds, the compounds of the present invention may also be used as salts with various countercations to yield an orally available formulation. Such pharmaceutically acceptable cations may be amongst others mono- or bivalent ions such as ammonium, the alkaline metals sodium or potassium or the alkaline earth metals magnesium or calcium, certain pharmaceutically acceptable amines such as tris(hydroxymethyl)aminomethane, ethylendiamine, diethylamine, piperazine or others, or certain cationic amino acids such as lysine or arginine.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described above.

The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present invention is shown below. Unless otherwise indicated in the schemes, the variables have the same meaning as described above. The examples presented below are intended to illustrate particular embodiments of the invention. Suitable starting materials, building blocks and reagents employed in the synthesis as described below are commercially available from Sigma-Aldrich or Acros Organics, for example, or can be routinely prepared by procedures described in the literature, for example in "March's Advanced Organic Chemistry: Reactions, Mechanisms, and Structure", $5^{th}$ Edition; John Wiley & Sons or T. Eicher, S. Hauptmann "The Chemistry of Heterocycles; Structures, Reactions, Synthesis and Application", $2^{nd}$ edition, Wiley-VCH 2003; Fieser et al. "Fiesers' Reagents for organic Synthesis" John Wiley & Sons 2000.

EXAMPLES

Compounds of the present invention can be prepared by methods known to those who are skilled in the art. The following examples are only meant to represent examples of the invention and are in no way meant to be a limit of the invention.

Example 1: 5-(4-(2-Chloro-4-((5-cyclopropyl-3-(2, 6-dichlorophenyl)isoxazol-4-yl)methoxy)phenyl)-4-hydroxypiperidin-1-yl)-1-isopropyl-1H-pyrazole-3-carboxylic Acid (1)

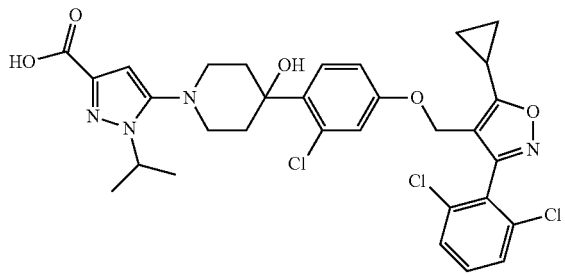 [SMILES: CC(C)n1nc(C(=O)O)cc1N1CCC(O)(c2ccc(OCc3c(-c4c(Cl)cccc4Cl)noc3C3CC3)cc2Cl)CC1]

Step 1: (Z)-Ethyl 2-hydroxy-4-oxo-4-(1,4-dioxa-8-azaspiro[4.5]decan-8-yl)but-2-enoate (1a)

To a suspension of 1-(1,4-dioxa-8-azaspiro[4.5]decan-8-yl)ethanone (4.0 g, 21.6 mmol) in dry THF (100 ml) was added t-BuLi (25 mL, 1.3M, 32.4 mmol) dropwise at −78° C. Then the reaction mixture was allowed to warm to rt, stirred for another 5 h, quenched with saturated aq. NH$_4$Cl. The mixture was extracted with EtOAc (100 mL×2), the organic layer was washed with H$_2$O (80 mL) and brine (80 mL), dried with Na$_2$SO$_4$, filtered, concentrated and the residue was purified by silica gel column (PE:EtOAc=5:1 to 2:1) to give the title compound as a colorless oil (4.6 g).

Step 2: Ethyl 1-isopropyl-5-(1,4-dioxa-8-azaspiro [4.5]decan-8-yl)-1H-pyrazole-3-carboxylate (1b)

To a suspension of intermediate 1a (2.0 g, 7.0 mmol), isopropylhydrazine monohydrochloride (1.0 g, 9.1 mmol) and pyridine (3 mL) in THF (40 ml) was added Lawesson's reagent (5.7 g, 14 mmol) portionwise at rt. The resulting mixture was heated to 60° C. and stirred for 16 h. Then EtOAc (50 mL) was added and the mixture was washed with sat. NaHCO$_3$ (50 m×2), aq. HCl (1M, 50 mL) and brine (50 mL). The organic phase was dried with Na$_2$SO$_4$, filtered, concentrated and the residue was purified by silica gel column (PE:EA=5:1 to 2:1) to give the title compound as a white solid (0.7 g).

Step 3: Ethyl 1-isopropyl-5-(4-oxopiperidin-1-yl)-1H-pyrazole-3-carboxylate (1c)

A suspension of intermediate 1b (0.70 g, 2.3 mmol, crude) in THF (10 ml) and H$_2$SO$_4$ (10%, 10 mL) was stirred for 16 h. The mixture was diluted with EtOAc (50 mL), washed with sat. NaHCO$_3$ (50 mL×2), aq. HCl (1M, 50 mL) and brine (50 mL). The organic phase was dried with Na$_2$SO$_4$, filtered, concentrated and the residue was purified by silica gel column (PE:EA=5:1 to 2:1) to give the title compound as a white solid. (0.61 g).

Step 4: Ethyl 5-(4-(4-((tert-butyldimethylsilyl)oxy)-2-chlorophenyl)-4-hydroxypiperidin-1-yl)-1-isopropyl-1H-pyrazole-3-carboxylate (1d)

To a round bottom flask was added LiCl (265 mg, 6.3 mmol), dry THF (10 ml) at rt and i-PrMgCl (1.9 ml, 2.0 M, 3.8 mmol) under N$_2$. The mixture was stirred at rt for 10 min, then a solution of (4-bromo-3-chlorophenoxy)(tert-butyl)dimethylsilane (1.1 g, 3.2 mol) in dry THF (2 ml) was added dropwise and stirring was continued at rt for another 1 hour. After that, the above reaction mixture was added into a solution of intermediate 1c (0.8 g, 2.9 mmol) in dry THF (10 ml) under N$_2$, and the mixture was stirred at rt for one hour. The reaction mixture was quenched with H$_2$O (20 mL), extracted with EtOAc (30 mL×3). The organic layer was washed with brine (20 mL), dried with Na$_2$SO$_4$, filtered and purified by column chromatography on silica gel (EA/PE=1/20) to give the title compound as a white solid (350 mg).

Step 5: Ethyl 5-(4-(2-chloro-4-hydroxyphenyl)-4-hydroxypiperidin-1-yl)-1-isopropyl-1H-pyrazole-3-carboxylate (1e)

To a suspension of intermediate 1d (0.3 g, 0.67 mmol) in THF (5 ml) was added TBAF (277 mg, 1.01 mmol) at rt and the mixture was stirred at rt for 30 min. Then the mixture was quenched with water (20 mL), extracted with EtOAc (20 mL×3). The organic phase was washed with brine (20 mL), dried with Na$_2$SO$_4$, filtered and concentrate to give the title compound as a white solid, which was used directly in next step without further purification (0.23 g).

Step 6: Ethyl 5-(4-(2-chloro-4-((5-cyclopropyl-3-(2, 6-dichlorophenyl)isoxazol-4-yl)methoxy)phenyl)-4-hydroxypiperidin-1-yl)-1-isopropyl-1H-pyrazole-3-carboxylate (1f)

To a suspension of intermediate 1e (230 mg, 0.56 mol), (5-cyclopropyl-3-(2,6-dichlorophenyl)isoxazol-4-yl)methanol (158 mg, 0.56 mol) and PPh$_3$ (239 mg, 1.1 mmol) in toluene (10 ml) was added DIAD (226 mg, 1.1 mmol) dropwise at 0° C. The resulting mixture was stirred at rt for 4 h. The reaction mixture was diluted with H$_2$O, extracted with EtOAc (20 mL×3) and the organic layers were concentrated to dryness. The residue was and purified by preparative TLC (EtOAc/PE=1/1) to give the title compound as a white solid (220 mg).

Step 7: 5-(4-(2-Chloro-4-((5-cyclopropyl-3-(2,6-dichlorophenyl)isoxazol-4-yl)methoxy)phenyl)-4-hydroxypiperidin-1-yl)-1-isopropyl-1H-pyrazole-3-carboxylic Acid (1)

A suspension of intermediate 1f (180 mg, 0.267 mmol) in MeOH (10 mL) and aq. NaOH (10%, 10 mL) was stirred at 30° C. for 4 h. The mixture was concentrated under reduced pressure, HCl (1M) was added until pH=2-3 and the resulting precipitate was filtered off and dried under vacuum to give Example 1 as a white solid (100 mg). $^1$H-NMR (400 MHz, CD$_3$Cl): δ ppm 7.43-7.39 (m, 3H), 7.36-7.31 (m, 1H), 6.83 (d, J=2.0 Hz, 1H), 6.72 (dd, J=8.8 Hz, 2.0 Hz, 1H), 6.51 (s, 1H), 4.81 (s, 2H), 4.71-4.65 (m, 1H), 3.29-3.25 (m, 2H), 2.98-2.93 (m, 2H), 2.2.45-2.37 (m, 2H), 2.17-2.05 (m, 3H), 1.47 (d, J=6.0 Hz, 6H), 1.32-1.25 (m, 2H), 1.18-1.12 (m, 2H). MS-ESI: m/z 645.3/647.3 [M+H]$^+$ 667.3/669.3 [M+Na]$^+$.

If one were to use a similar procedure as described above, the following compounds can be prepared:

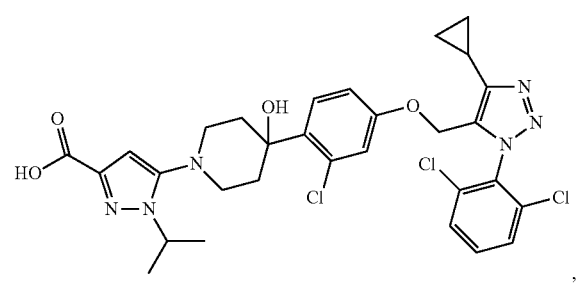
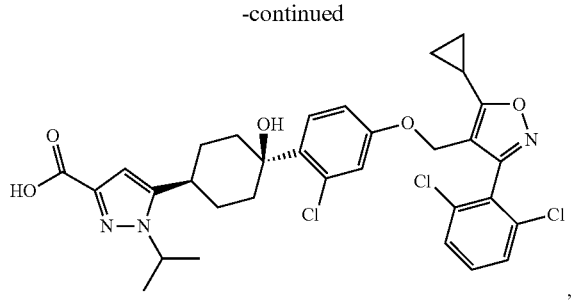
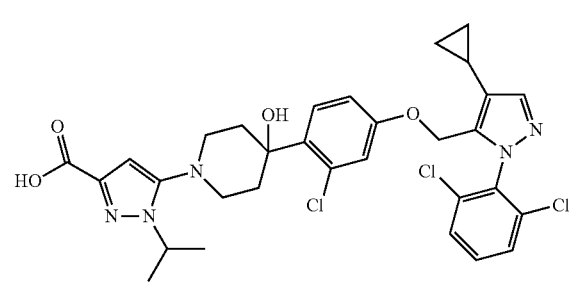
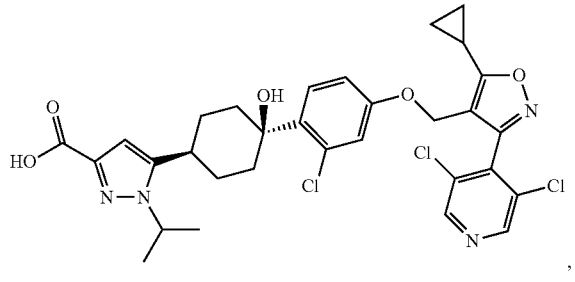
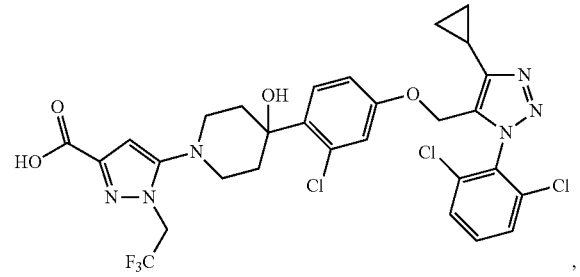
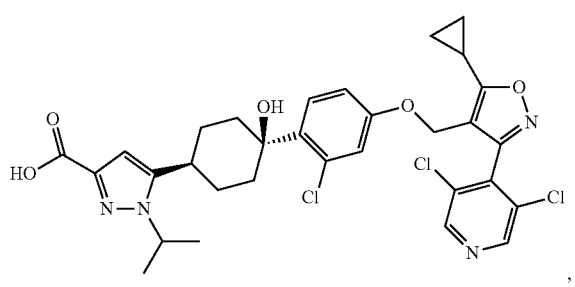
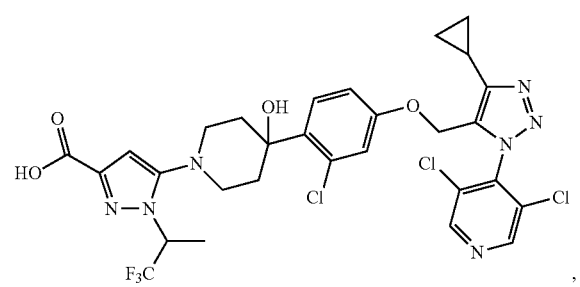
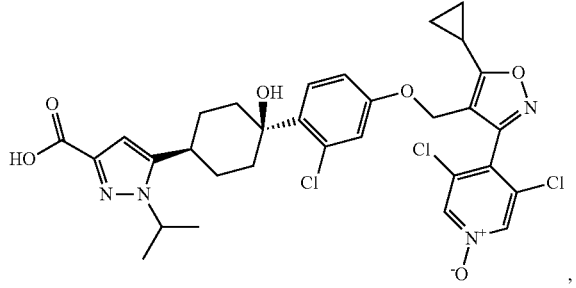
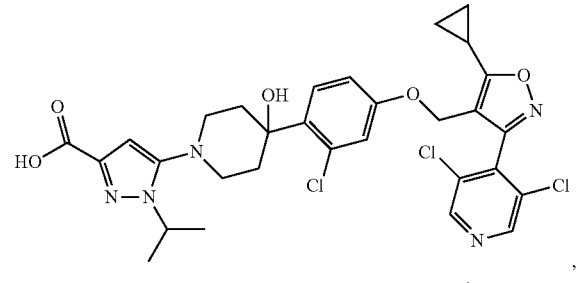
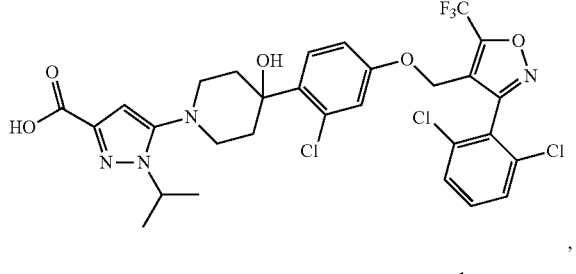
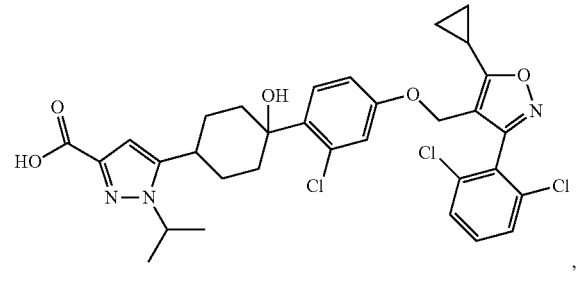
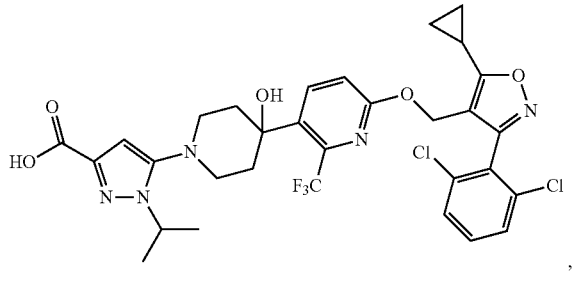

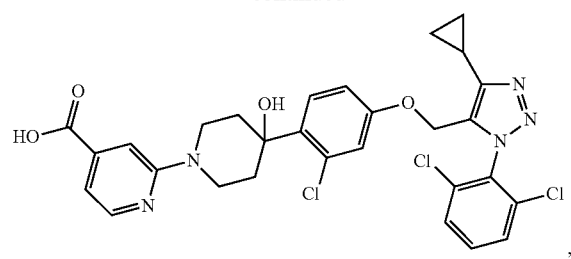
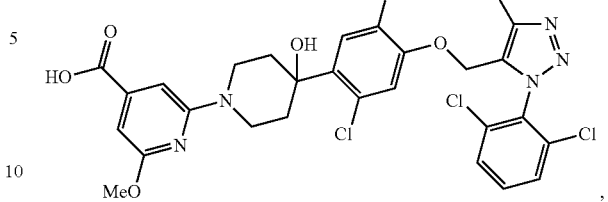
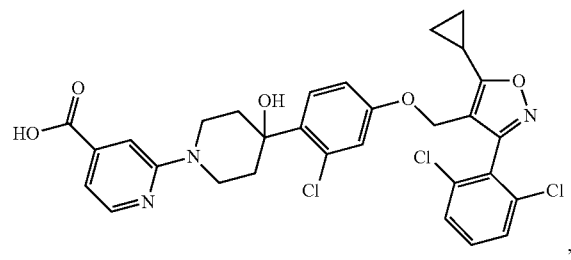
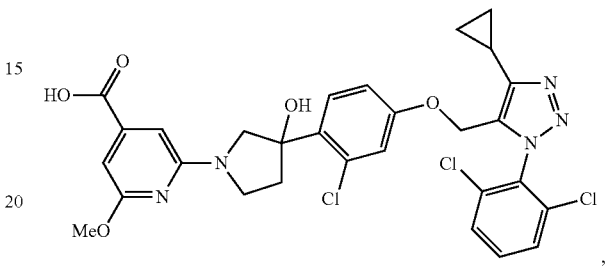
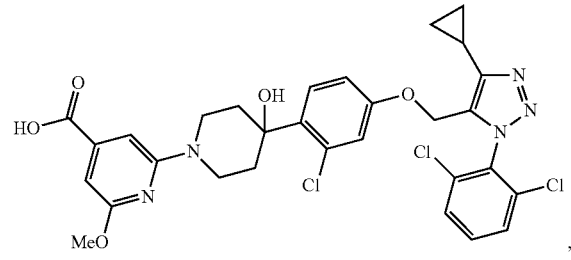
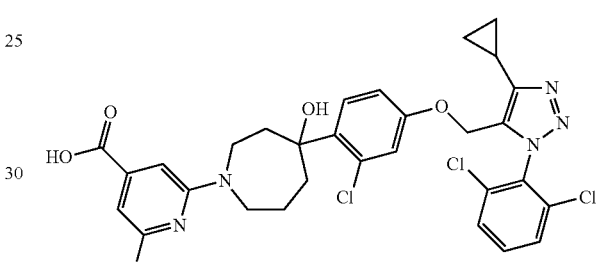
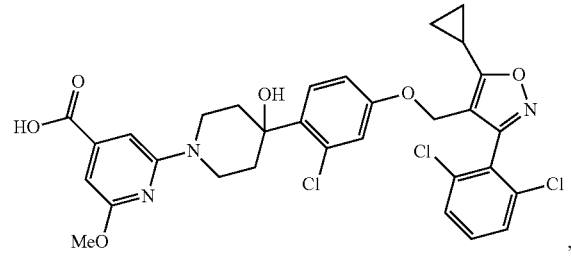
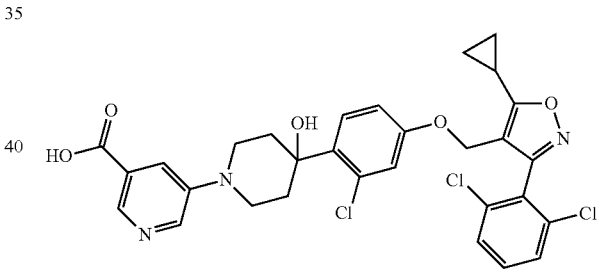
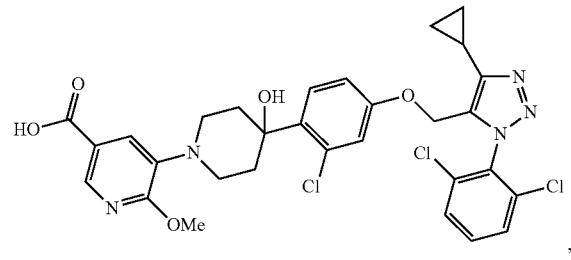
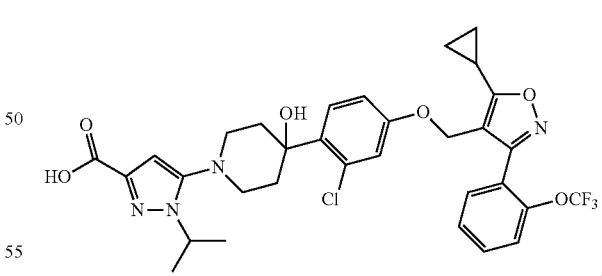
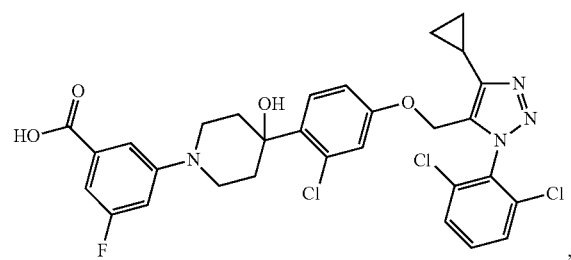
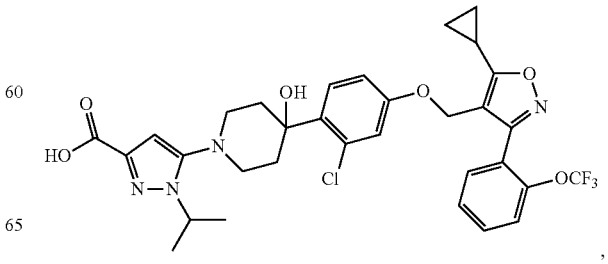

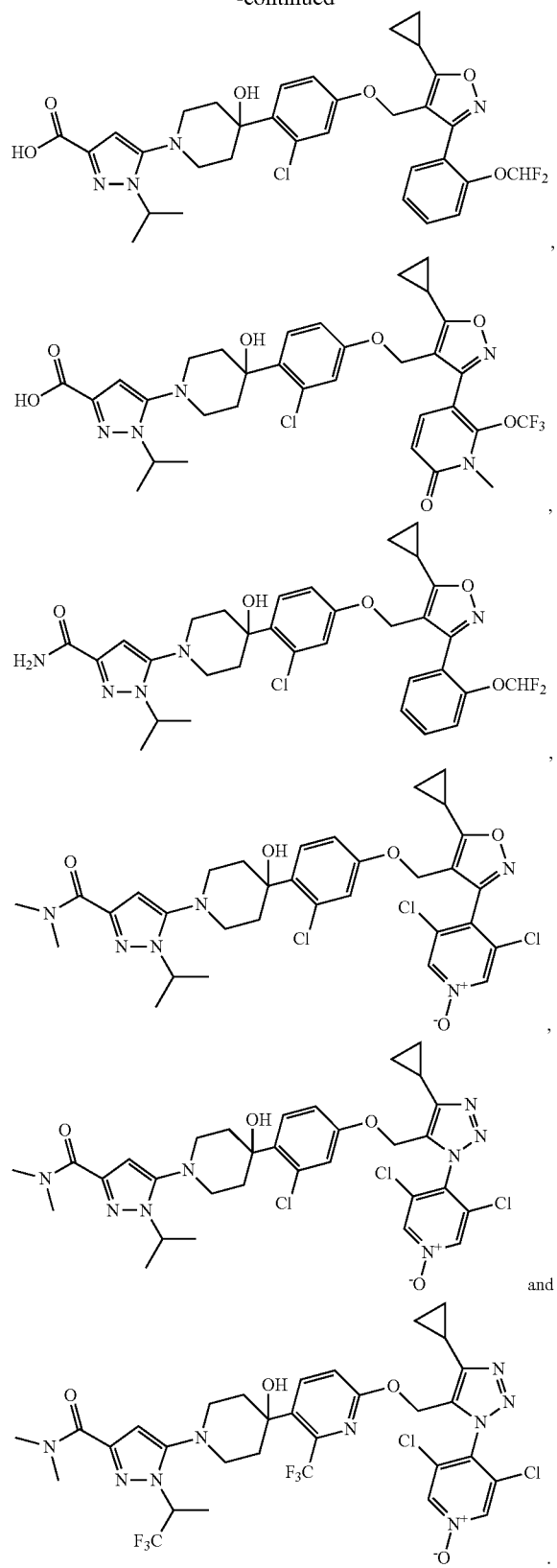

Assays
FRET Activity Assay Determination of a ligand mediated cofactor peptide interaction to quantify ligand binding to the nuclear receptor FXR was performed as follows: Preparation of human FXR alpha ligand binding domain: The human FXRalpha LBD was expressed in *E. coli* strain BL21 (DE3) as an N-terminally GST tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed *E. coli* strain was diluted 1:20 in LB-Ampicillin medium and grown at 30° C. to an optical density of $OD_{600}$=0.4-0.6. Gene expression was then induced by addition of 0.5 mM IPTG. Cells were incubated an additional 6 h at 30° C., 180 rpm. Cells were collected by centrifugation (7000×g, 7 min, rt). Per liter of original cell culture, cells were resuspended in 10 mL lysis buffer (50 mM Glucose, 50 mM Tris pH 7.9, 1 mM EDTA and 4 mg/mL lysozyme) and left on ice for 30 min. Cells were then subjected to sonication and cell debris removed via centrifugation (22000×g, 30 min, 4° C.). Per 10 mL of supernatant 0.5 mL prewashed Glutathione 4B sepharose slurry (Qiagen) was added and the suspension kept slowly rotating for 1 h at 4° C. Glutathione 4B sepharose beads were pelleted by centrifugation (2000×g, 15 sec, 4° C.) and washed twice in wash buffer (25 mM Tris, 50 mM KCl, 4 mM $MgCl_2$ and 1M NaCl). The pellet was resuspended in 3 mL elution buffer per liter of original culture (elution buffer: 20 mM Tris, 60 mM KCl, 5 mM $MgCl_2$ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM $MgCl_2$ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B-CPSSHSSLTERHKILHRLLQEGSPS-COOH where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 μL in a 384 well plate, in a Tris-based buffer (20 mM Tris-HCl pH 7.5; 60 mM KCl, 5 mM $MgCl_2$; 35 ng/μL BSA), containing 20-60 ng/well recombinantly expressed FXR-LBD fused to GST, 200-600 nM N-terminally biotinylated peptide, representing SRC1 aminoacids 676-700, 200 ng/well Streptavidin-xl-APC conjugate (Prozyme) and 6-10 ng/well Eu W1024-antiGST (Perkin Elmer). DMSO content of the samples was kept at 1%. After generation of the assay mix and diluting the potentially FXR modulating ligands, the assay was equilibrated for 1 h in the dark at rt in FIA-plates black 384 well (Greiner). The LANCE signal was detected by a Perkin Elmer VICTOR2VTM Multilabel Counter. The results were visualized by plotting the ratio between the emitted light at 665 and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal. The compound of Example 1 shows an agonistic potential of $EC_{50} < 25$ nM.

Mammalian One Hybrid (M1H) Assay

Determination of a ligand mediated Gal4 promoter driven transactivation to quantify ligand binding mediated activation of FXR was performed as follows: The cDNA part encoding the FXR ligand binding domain was cloned into vector pCMV-BD (Stratagene) as a fusion to the yeast GAL4 DNA binding domain under the control of the CMV promoter. The amino acid boundaries of the ligand binding domain were amino acids 187-472 of Database entry NM_005123 (RefSeq). The plasmid pFR-Luc (Stratagene) was used as the reporter plasmid, containing a synthetic promoter with five tandem repeats of the yeast GAL4 binding sites, driving the expression of the *Photinus pyralis* (American firefly) luciferase gene as the reporter gene. In order to improve experimental accuracy the plasmid pRL-CMV (Promega) was cotransfected. pRL-CMV contains the constitutive CMV promoter, controlling the expression of the *Renilla reniformis* luciferase. All Gal4 reporter gene assays were done in HEK293 cells (obtained from DSMZ, Braunschweig, Germany) grown in MEM with L-Glutamine and Earle's BSS supplemented with 10% fetal bovine serum, 0.1 mM nonessential amino acids, 1 mM sodium pyruvate, and 100 units Penicilin/Streptavidin per mL at 37° C. in 5% $CO_2$. Medium and supplements were obtained from Invitrogen. For the assay, $5 \times 10^5$ cells were plated per well in 96 well plates in 100 µL per well MEM without Phenol Red and L-Glutamine and with Earle's BSS supplemented with 10% charcoal/dextran treated FBS (HyClone, South Logan, Utah), 0.1 mM nonessential amino acids, 2 mM glutamine, 1 mM sodium pyruvate, and 100 units Penicilin/Streptavidin per mL, incubated at 37° C. in 5% $CO_2$. The following day the cells were >90% confluence. Medium was removed and cells were transiently transfected using 20 µL per well of a OptiMEM-polyethylene-imine-based transfection-reagent (OptiMEM, invitrogen; Polyethyleneimine, Aldrich Cat No. 40,827-7) including the three plasmids described above. MEM with the same composition as used for plating cells was added 2-4 h after addition of transfection mixture. Then compound stocks, prediluted in MEM were added (final vehicle concentration not exceeding 0.1%). Cells were incubated for additional 16 h before firefly and *renilla* luciferase activities were measured sequentially in the same cell extract using a Dual-Light-Luciferase-Assay system (Dyer et al., Anal. Biochem. 2000, 282, 158-161). All experiments were done in triplicates.

The invention claimed is:

1. A compound according to the following Formula (1), an enantiomer, diastereomer, tautomer, solvate, or pharmaceutically acceptable salt thereof $$R-A-Y-B(R^4)_n-Q-O-Z \text{ with OH on B}  \quad (1)$$

wherein

R is selected from the group consisting of hydrogen, halogen, $C_{1-6}$-alkyl, $C_{2-6}$-alkenyl, $C_{2-6}$-alkynyl, halo-$C_{1-6}$-alkyl, $C_{0-6}$-alkylene-$R^7$, $C_{0-6}$-alkylene-O—$R^7$, $C_{0-6}$-alkylene-CN, $C_{0-6}$-alkylene-$NR^7R^8$, O—$C_{3-10}$-cycloalkyl, O—$C_{1-6}$-alkylene-O—$R^7$, O—$C_{3-10}$-heterocycloalkyl, $C_{0-6}$-alkylene-$CO_2R^7$, $C_{0-6}$-alkylene-C(O)$R^7$, $C_{0-6}$-alkylene-C(O)$NR^7R^8$, $C_{0-6}$-alkylene-C(O)$NR^7SO_2R^7$, $C_{0-6}$-alkylene-N($R^7$)C(O)$R^7$, $C_{0-6}$-alkylene-SO$_x$—$R^7$, $C_{0-6}$-alkylene-SO$_3$H, $C_{0-6}$-alkylene-SO$_2$—$NR^7R^8$, $C_{0-6}$-alkylene-SO$_2$—$NR^8COR^7$, $C_{0-6}$-alkylene-N($R^7$)SO$_2$—$R^8$, and $C_{0-6}$-alkylene-SO$_2$—$C_{3-10}$-heterocycloalkyl, wherein alkylene, cycloalkyl, heterocycloalkyl and the 5- or 6-membered heteroaryl are unsubstituted or substituted by 1 to 4 substituents independently selected from the group consisting of halogen, CN, $C_{1-3}$-alkyl, halo-$C_{1-3}$-alkyl, OH, oxo, $CO_2H$, $SO_3H$, O—$C_{1-3}$-alkyl and O-halo-$C_{1-3}$-alkyl;

$R^7$ is independently selected from the group consisting of hydrogen, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and phenyl, wherein alkyl, alkylene, cyclolalkyl, heterocycloalkyl, phenyl and heteroaryl are unsubstituted or substituted with 1 to 6 substituents independently selected from the group consisting of halogen, CN, OH, oxo, $CO_2H$, $C_{1-3}$-alkyl, halo-$C_{1-3}$-alkyl, O—$C_{1-3}$-alkyl, O-halo-$C_{1-3}$-alkyl, $SO_3H$ and $SO_2$—$C_{1-3}$-alkyl;

$R^8$ is independently selected from the group consisting of hydrogen, $C_{1-6}$-alkyl, halo-$C_{1-6}$-alkyl and $C_{3-6}$-cycloalkyl;

or $R^7$ and $R^8$ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, $C_{1-4}$-alkyl and halo-$C_{1-4}$-alkyl;

A is a 6-10 membered mono- or bicyclic aryl or a 5-10 membered mono- or bicyclic heteroaryl containing 1 to 5 heteroatoms independently selected from the group consisting of N, O and S, wherein aryl and heteroaryl are unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl;

B is a $C_{5-8}$-cycloalkyl ring or, if Y is N, then is B a $C_{4-8}$-heterocycloalkyl or bridged $C_{4-8}$-heterocycloalkyl containing one nitrogen atom, and wherein the substituent Q is not directly adjacent to substituent A;

Q is selected from the group consisting of phenyl, pyridyl, thiazolyl, thiophenyl, pyrimidyl, oxazolyl, pyrazolyl, imidazolyl and triazolyl, each unsubstituted or substituted with one or two groups independently selected from the group consisting of halogen, $C_{1-4}$-alkyl, halo-$C_{1-4}$-alkyl, $C_{1-4}$-alkoxy or halo-$C_{1-4}$-alkoxy;

Y is selected from N, CH or CF;

Z is selected from

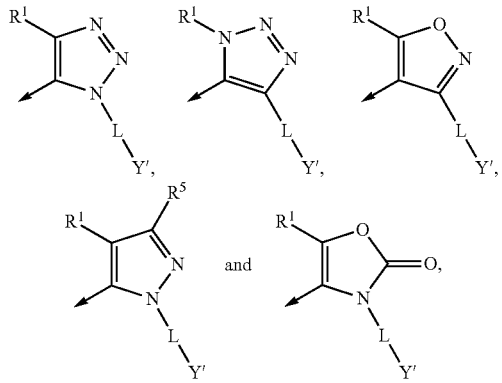

wherein

L is selected from the group consisting of a bond, $C_{1-3}$-alkylene and $C_{1-3}$-alkylene-O—;

Y' is selected from phenyl, pyridyl, pyridyl-N-oxide, pyrimidyl, pyridinonyl, pyrimidinonyl, $C_{4-8}$-cycloalkyl, and $C_{4-8}$-heterocycloalkyl, wherein phenyl, pyridyl, pyridyl-N-oxide, pyrimidyl, pyridinonyl, pyrimidinonyl, $C_{4-8}$-cycloalkyl and $C_{4-8}$-heterocycloalkyl are substituted with $R^2$ and $R^3$ and optionally substituted one or two times with a group selected from fluoro, chloro, CN, $NH_2$, $NH(C_{1-3}$-alkyl), $N(C_{1-3}$-alkyl)$_2$, $C_{1-3}$-alkyl, fluoro-$C_{1-3}$-alkyl, OH, $C_{1-3}$-alkoxy, fluoro-$C_{1-3}$-alkoxy, $C_{3-6}$-cycloalkyl and fluoro-$C_{3-6}$-cycloalkyl;

$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_{3-6}$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;

$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl;

$R^4$ is independently selected from halogen, $C_{1-3}$-alkyl, halo-$C_{1-3}$-alkyl, $C_{1-3}$-alkoxy, halo-$C_{1-3}$-alkoxy, $C_{3-6}$-cycloalkyl, and fluoro-$C_{3-6}$-cycloalkyl;

$R^5$ is selected from the group consisting of hydrogen, fluoro, $CH_3$, $CHF_2$ and $CF_3$;

n is selected from 0, 1, 2, 3 and 4; and x is selected from 0, 1 and 2.

2. The compound according to claim 1 wherein

R is selected from the group consisting of $CO_2H$, $SO_3H$, $CONR^7R^8$, tetrazolyl, 1,2,4-oxadiazol-5(4H)-one-3-yl and $SO_2NHCOR^7$;

$R^7$ selected from the group consisting of hydrogen, $C_{1-6}$-alkyl, halo-$C_{1-6}$-alkyl, $C_{1-6}$-alkylene-$R^9$, $SO_2$—$C_{1-3}$-alkyl;

$R^8$ selected from the group consisting of hydrogen, $C_{1-6}$-alkyl, halo-$C_{1-6}$-alkyl; and $R^9$ is selected from the group consisting of COOH, OH and $SO_3H$.

3. The compound according to claim 1 wherein

A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, oxazolyl, naphthyl, quinolyl, isoquinolyl, benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl.

4. The compound according to claim 1 wherein R-A is selected from

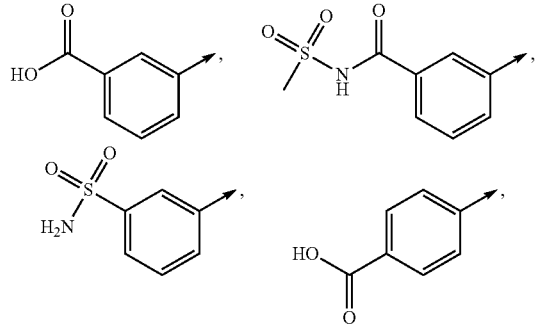

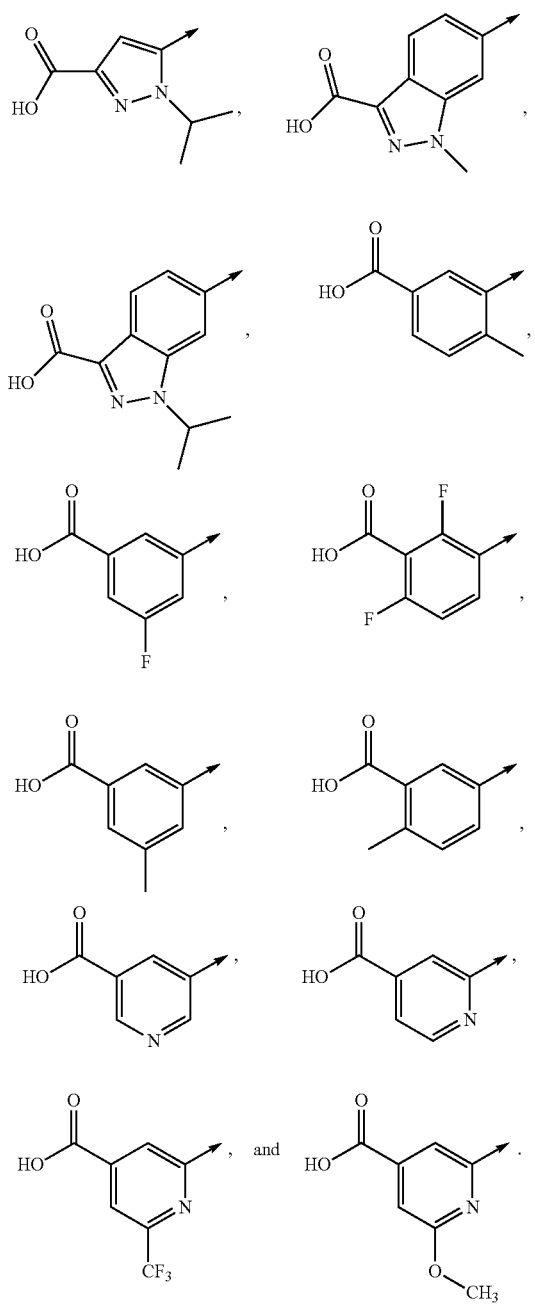

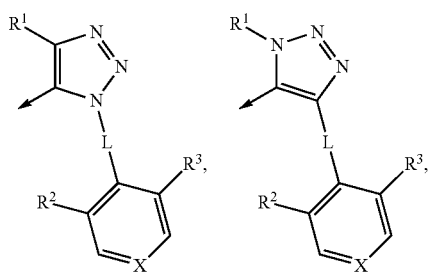

5. The compound according to claim 1 wherein Z is selected from

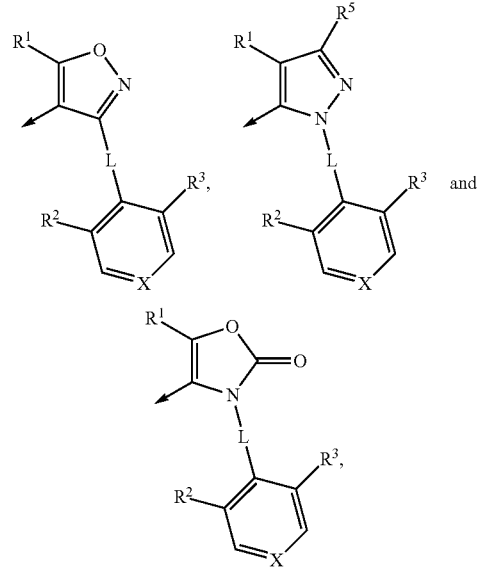

wherein
L is selected from the group consisting of a bond, $C_{1-3}$-alkylene and $C_{1-3}$-alkylene-O—;
X is selected from the group consisting of CH, CF, N and NO;
$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_{3-6}$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;
$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl; and
$R^5$ is selected from the group consisting of hydrogen, fluoro, $CH_3$, $CHF_2$ and $CF_3$.

6. The compound according to claim 1 wherein Z is selected from

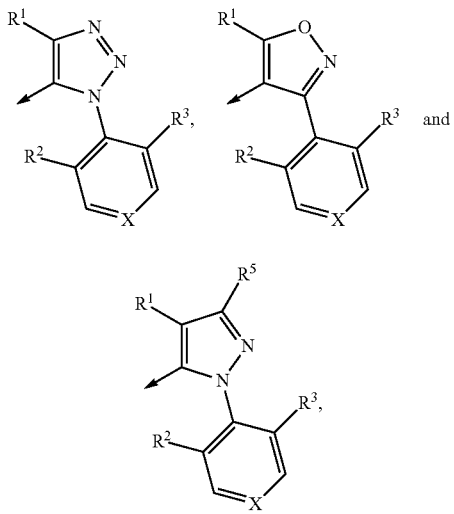

wherein

X is selected from the group consisting of CH, CF, N and NO;

$R^1$ is selected from the group consisting of $CF_3$, $CHF_2$, isopropyl and cyclopropyl, wherein isopropyl and cyclopropyl are unsubstituted or substituted with one or two fluoro or one hydroxy;

$R^2$ is selected from the group consisting of fluoro, chloro, $CH_3$, $CHF_2$, $CF_3$, $OCHF_2$ and $OCF_3$;

$R^3$ is selected from the group consisting of hydrogen, fluoro, chloro, $CH_3$, $CHF_2$, $CF_3$, $OCHF_2$ and $OCF_3$; and $R^5$ is selected from the group consisting of hydrogen, fluoro, $CH_3$, $CHF_2$ and $CF_3$.

7. The compound according to claim 1 wherein

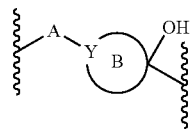

is selected from

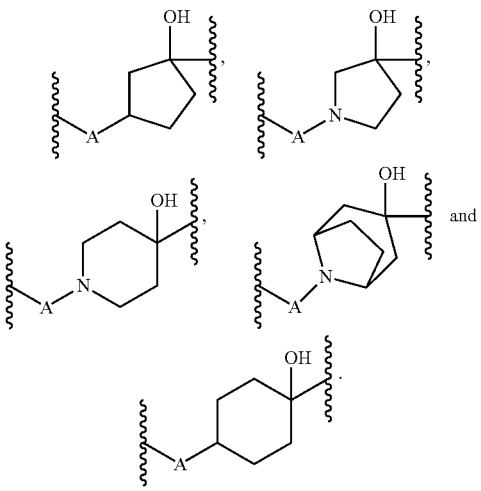

8. The compound according to claim 1 with Formula (2)

(2)

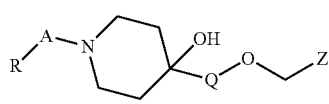

wherein

A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, oxazolyl, naphthyl, quinolyl, isoquinolyl, benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl;

R is selected from the group consisting of $CO_2H$, $SO_3H$, $CONR^7R^8$, tetrazolyl, 1,2,4-oxadiazol-5(4H)-one-3-yl and $SO_2NHCOR^7$, wherein $R^7$ selected from the group consisting of hydrogen, $C_{1-6}$-alkyl, halo-$C_{1-6}$-alkyl, $C_{1-6}$-alkylene-$R^9$, $SO_2$—$C_{1-6}$-alkyl;

$R^8$ selected from the group consisting of hydrogen, $C_{1-6}$-alkyl, halo-$C_{1-6}$-alkyl; and $R^9$ is selected from the group consisting of COOH, OH and $SO_3H$;

Q is selected from the group consisting of phenyl, pyridyl, thiazolyl, thiophenyl and pyrimidyl, each unsubstituted or substituted with one or two groups independently selected from the group consisting of fluoro, chloro, $CH_3$, $CHF_2$ and $CF_3$;

Z is selected from

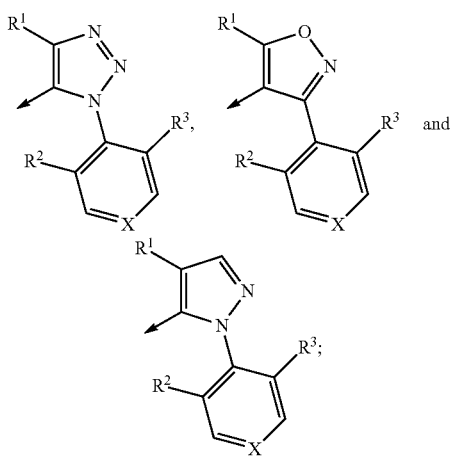

X is selected from the group consisting of CH, N and NO;

$R^1$ is selected from the group consisting of isopropyl and cyclopropyl, wherein isopropyl and cyclopropyl are unsubstituted or substituted with one or two fluoro or one hydroxy;

$R^2$ is selected from the group consisting of fluoro, chloro, $CH_3$, $CHF_2$, $CF_3$, $OCHF_2$ and $OCF_3$; and $R^3$ is selected from the group consisting of hydrogen, fluoro, chloro, $CH_3$, $CHF_2$, $CF_3$, $OCHF_2$ and $OCF_3$.

9. The compound according to any of claim 1 with Formula (3)

(3)

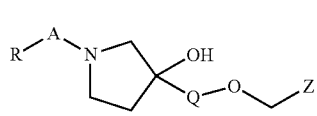

wherein

A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, oxazolyl, naphthyl, quinolyl, isoquinolyl, benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl;

R is selected from the group consisting of $CO_2H$, $SO_3H$, $CONR^7R^8$, tetrazolyl, 1,2,4-oxadiazol-5(4H)-one-3-yl and $SO_2NHCOR^7$, wherein R[7] selected from the group consisting of hydrogen, $C_{1-6}$-alkyl, halo-$C_{1-6}$-alkyl, $C_{1-6}$-alkylene-R[9], $SO_2$—$C_{1-6}$-alkyl;

R[8] selected from the group consisting of hydrogen, $C_{1-6}$-alkyl, halo-$C_{1-6}$-alkyl; and R[9] is selected from the group consisting of COOH, OH and $SO_3H$;

Q is selected from the group consisting of phenyl, pyridyl, thiazolyl, thiophenyl and pyrimidyl, each unsubstituted or substituted with one or two groups independently selected from the group consisting of fluoro, chloro, $CH_3$, $CHF_2$ and $CF_3$;

Z is selected from

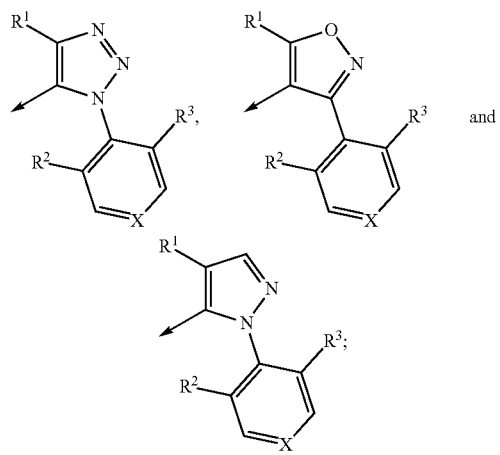

X is selected from the group consisting of CH, N and NO;

R[1] is selected from the group consisting of isopropyl and cyclopropyl, wherein isopropyl and cyclopropyl are unsubstituted or substituted with one or two fluoro or one hydroxy;

R[2] is selected from the group consisting of fluoro, chloro, $CH_3$, $CHF_2$, $CF_3$, $OCHF_2$ and $OCF_3$; and R[3] is selected from the group consisting of hydrogen, fluoro, chloro, $CH_3$, $CHF_2$, $CF_3$, $OCHF_2$ and $OCF_3$.

10. A compound selected from the group consisting of:

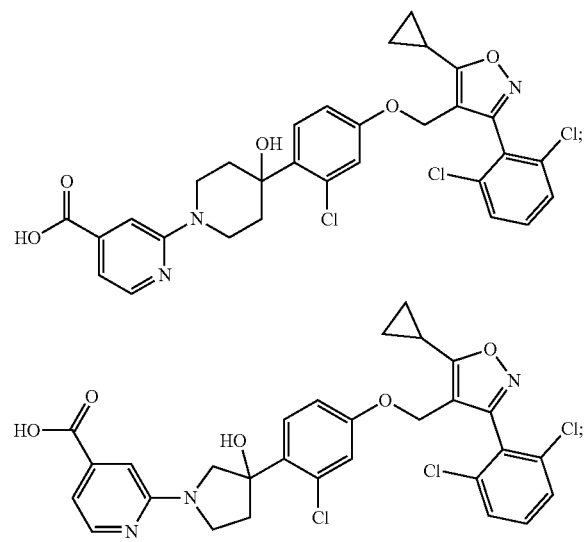

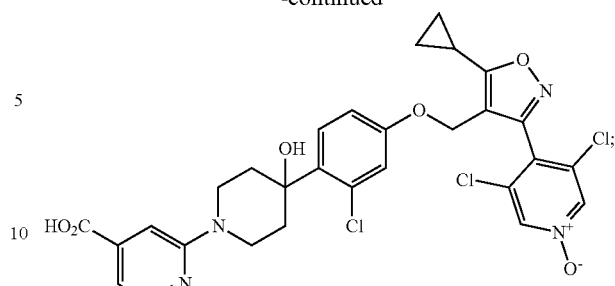

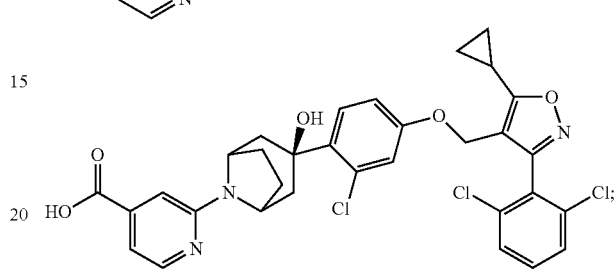

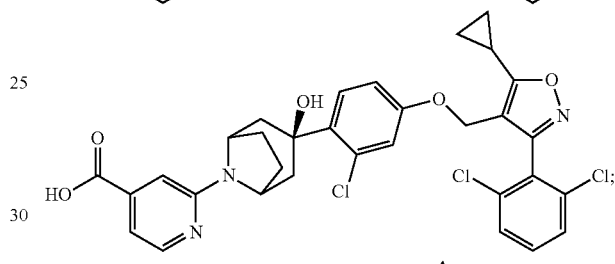

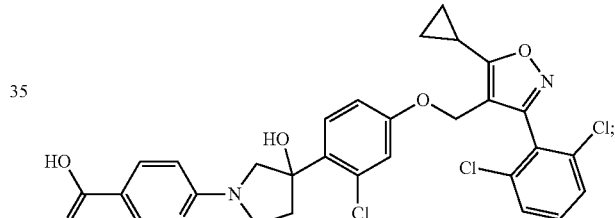

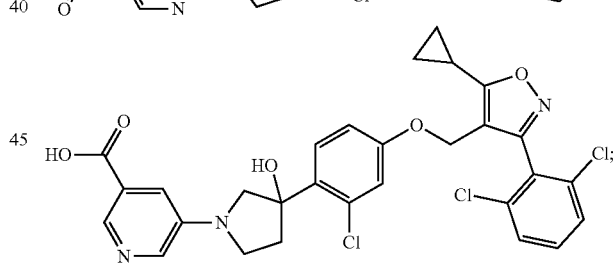

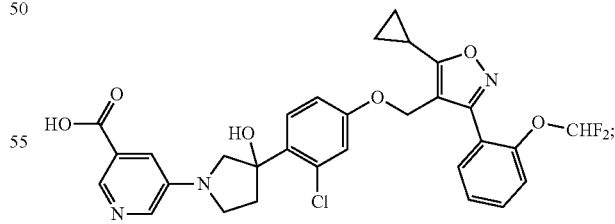

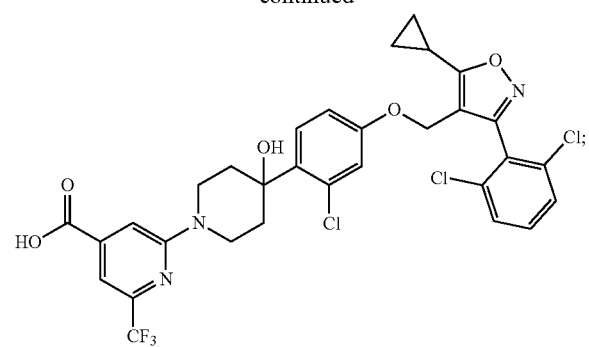
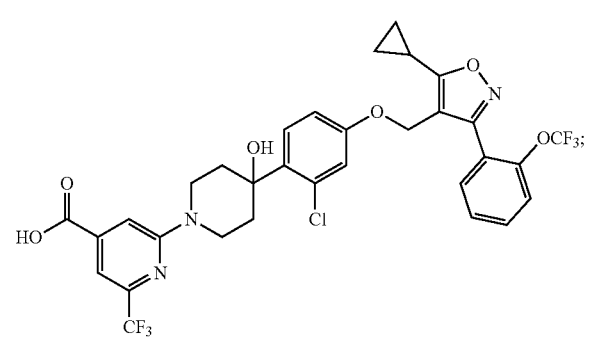
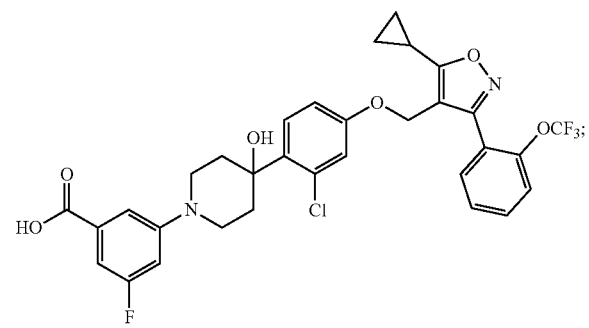
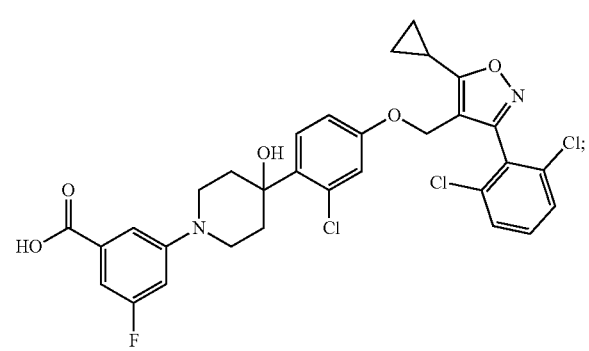
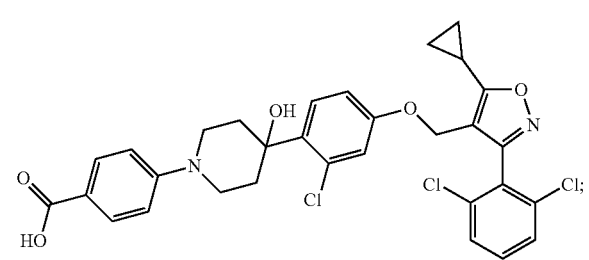
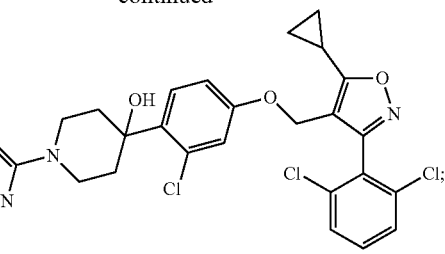
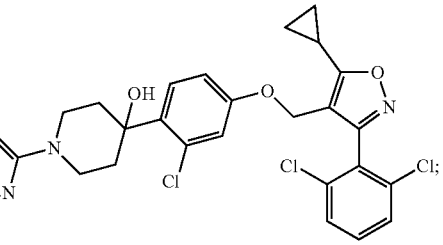
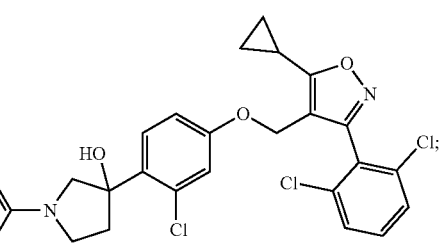
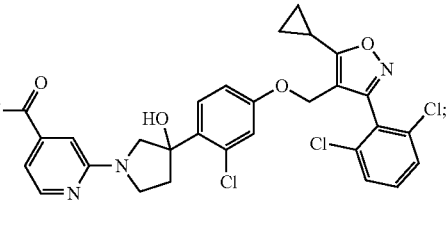
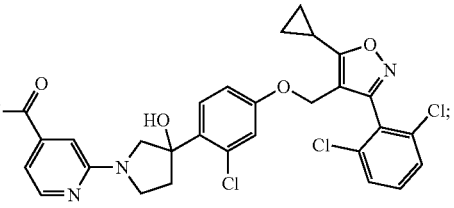
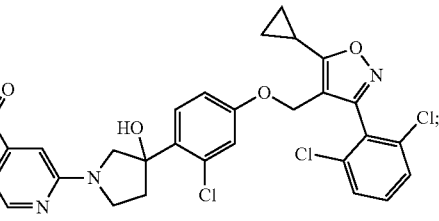
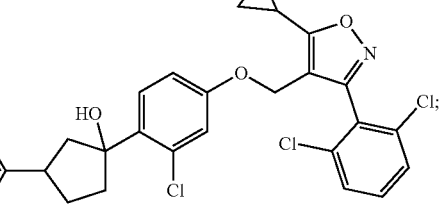

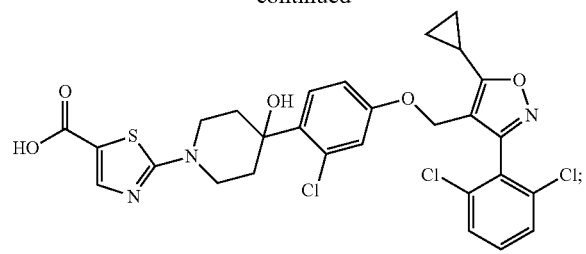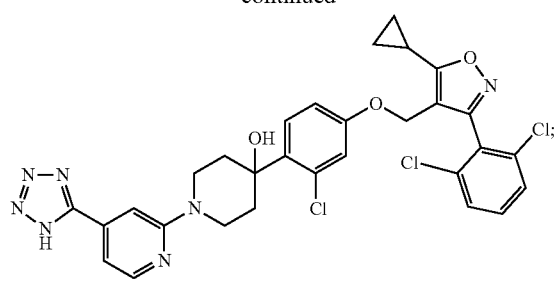
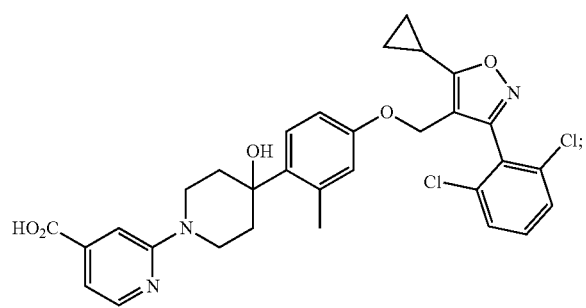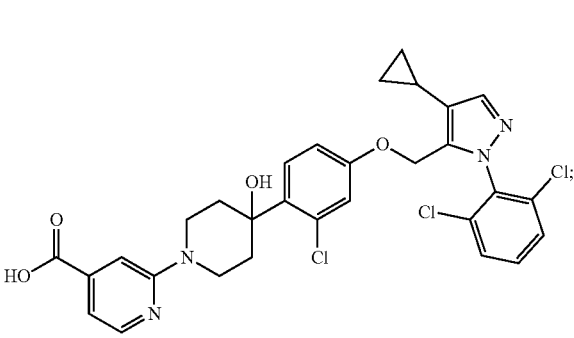
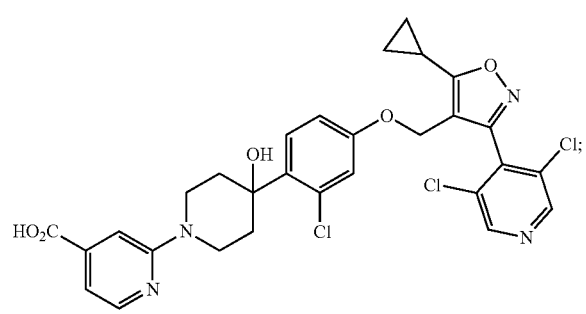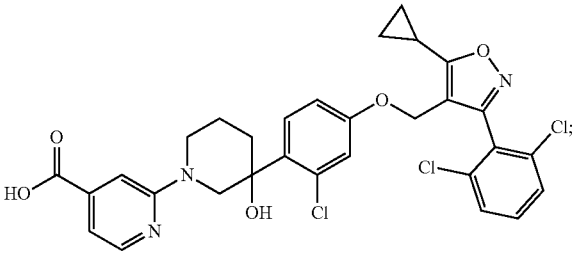
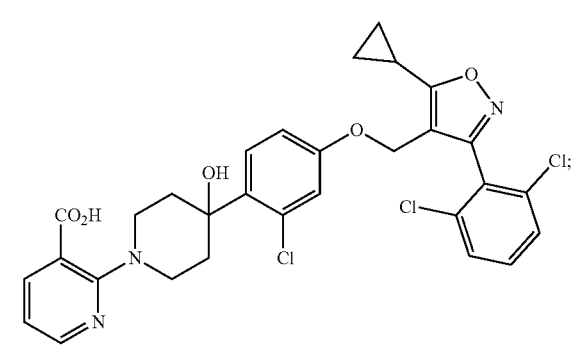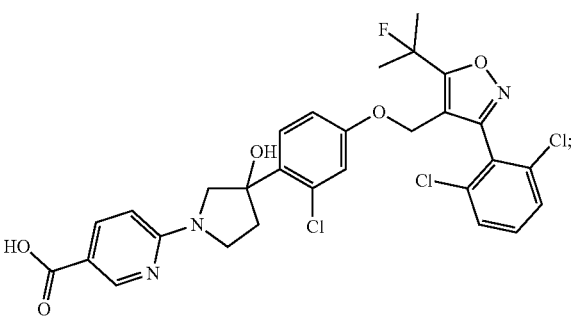
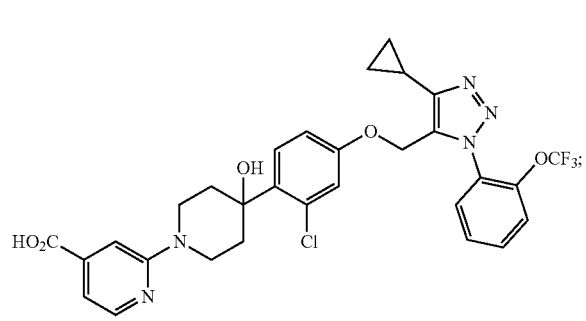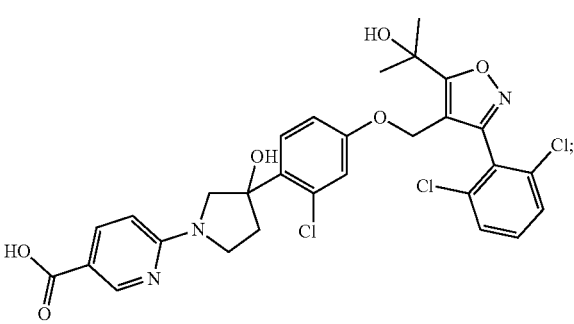

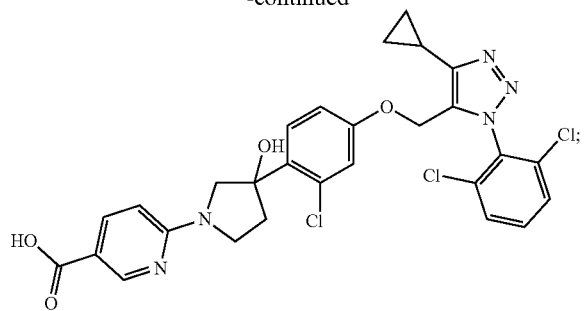

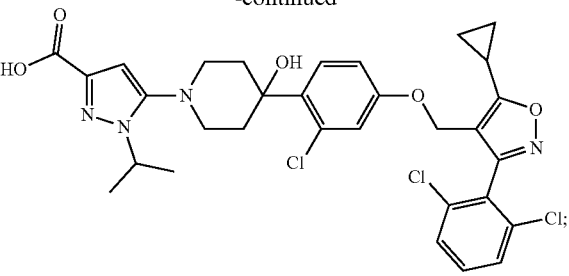

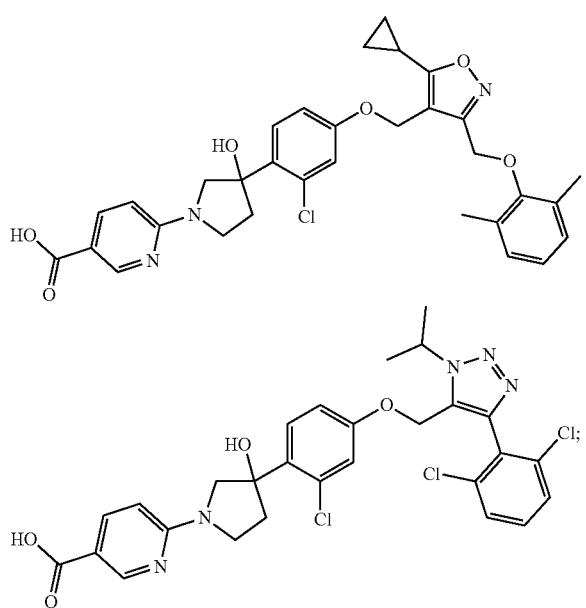

and or an enantiomer, diastereomer, tautomer, solvate, or pharmaceutical acceptable salt thereof.

11. A method of treating a patient having an FXR mediated condition selected from the group consisting of liver fibrosis, obstructive or chronic inflammatory disorders of the liver, liver cirrhosis, liver steatosis, cholestatic or fibrotic effects that are associated with alcohol-induced cirrhosis or with viral-borne forms of hepatitis, liver failure or liver ischemia after major liver resection, chemotherapy associated steatohepatitis (CASH), acute liver failure, and inflammatory bowel diseases, the method comprising administering a compound of claim 1 or an enantiomer, diastereomer, tautomer, solvate, or pharmaceutically acceptable salt thereof, to a patient in need thereof.

12. A method of treating a patient having an FXR mediated condition selected from the group consisting of type II diabetes, diabetic nephropathy, diabetic neuropathy, diabetic retinopathy, observed effects of clinically manifest long term diabetes, non-alcoholic fatty liver disease (NAFLD), non-alcoholic steatohepatitis (NASH), obesity, metabolic syndrome, acute myocardial infarction, and acute stroke or thrombosis which occurs as an endpoint of chronic obstructive atherosclerosis, the method comprising administering a compound of claim 1 or an enantiomer, diastereomer, tautomer, solvate, or pharmaceutically acceptable salt thereof, to a patient in need thereof.

* * * * *